US007638482B2

(12) United States Patent
LaVallie et al.

(10) Patent No.: US 7,638,482 B2
(45) Date of Patent: Dec. 29, 2009

(54) PROTEIN KINASE C ZETA AS A DRUG TARGET FOR ARTHRITIS AND OTHER INFLAMMATORY DISEASES

(75) Inventors: Edward R. LaVallie, Harvard, MA (US); Lisa A. Collins-Racie, Acton, MA (US); Maya Arai, Brookline, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/842,142

(22) Filed: May 10, 2004

(65) Prior Publication Data

US 2004/0259136 A1     Dec. 23, 2004

Related U.S. Application Data

(60) Provisional application No. 60/468,987, filed on May 8, 2003, provisional application No. 60/491,274, filed on Jul. 31, 2003.

(51) Int. Cl.
*A61K 38/00* (2006.01)
*A61K 38/02* (2006.01)
*A61K 48/00* (2006.01)
*C12N 5/22* (2006.01)
*A61K 38/04* (2006.01)

(52) U.S. Cl. .............................. 514/2; 514/44; 435/375
(58) Field of Classification Search ................. 514/825, 514/169, 2, 44
See application file for complete search history.

(56) References Cited

U.S. PATENT DOCUMENTS

| 5,565,448 | A  | * | 10/1996 | Nambi et al. ................ 514/215 |
| 6,368,831 | B1 | * | 4/2002  | Maurer et al. ............... 435/69.2 |
| 6,506,559 | B1 |   | 1/2003  | Fire et al. |
| 6,608,105 | B2 | * | 8/2003  | Asakawa et al. ............ 514/460 |
| 2003/0105075 | A1 | * | 6/2003 | Meijer .................... 514/212.07 |

FOREIGN PATENT DOCUMENTS

WO     WO 0100229 A1 * 1/2001

OTHER PUBLICATIONS

Goldring et al. Interleukin-1 beta-modulated gene expression in immortalized human chondrocytes. J Clin Invest. vol. 94, No. 6, pp. 2307-2316, Dec. 1994.*
Theiler et al. Clinical, biochemical and imaging methods of assessing osteoarthritis and clinical trials with agents claiming , 'chondromodulating' activity. Osteoarthritis Cartilage. vol. 2, No. 1, pp. 1-23, Mar. 1994.*
Lequesne et al. Guidelines for testing slow acting drugs in osteoarthritis. J Rheumatol Suppl. Supplement 41, pp. 65-71, Sep. 1994.*
Fajardo et al. Disease-modifying therapies for osteoarthritis : current status. Drugs Aging. vol. 22, No. 2, pp. 141-161, 2005.*
Toullec et al. The bisindolylmaleimide GF 109203X is a potent and selective inhibitor of protein kinase C. J Biol Chem. vol. 266, No. 24, pp. 15771-15781, Aug. 1991.*
van den Berg. Lessons from animal models of osteoarthritis. Curr Opin Rheumatol. vol. 13, No. 5, pp. 452-456, Sep. 2001.*
LaVallie et al. Protein kinase Czeta is up-regulated in osteoarthritic cartilage and is required for activation of NF-kappaB by tumor necrosis factor and interleukin-1 in articular chondrocytes. The Journal of Biological Chemistry, vol. 281, No. 34, pp. 24124-21437, Aug. 2006.*
Hamanishi et al. Protein kinase C activator inhibits progression of osteoarthritis induced in rabbit knee joints. J Lab Clin Med, vol. 127, No. 6, pp. 540-544, Jun. 1996.*
Thiam et al. Direct evidence of cytoplasmic delivery of PKC-alpha, -epsilon and -zeta pseudosubstrate lipopeptides: study of their implication in the induction of apoptosis. FEBS Letters, vol. 459, pp. 285-290, Oct. 1999.*
Piperno et al. Osteoarthritic cartilage fibrillation is associated with a decrease in chondrocyte adhesion to fibronectin. Osteoarthritis Cartilage. vol. 6, No. 6, pp. 393-399, Nov. 1998.*
Kim et al. p38 kinase-dependent and -independent inhibition of protein kinase c zeta and alpha regulates nitric oxide-induced apoptosis and dedifferentiation of articular chondrocytes. JBC Papers in Press, Published online on Jun. 4, 2002 as manuscript M205193200.*
Saraiva et al. Isoform-selectivity of PKC inhibitors acting at the regulatory and catalytic domain of mammalian PKC-alpha, -betaI, -delta, -eta, and -zeta. Journal of Enzyme Inhibition and Medicinal Chemistry, vol. 18, No. 6, pp. 475-483, Dec. 2003.*
Bonnet et al. Synthesis by chemoselective ligation and biological evaluation of novel cell-permeable PKC-Zeta pseudosubstrate lipopeptides. J. Med. Chem. vol. 44, pp. 468-471, 2001.*
Vuolteenaho et al. Effects of TNFalpha-antagonists on nitric oxide production in human cartilage. Osteoarthritis and Cartilage, vol. 10, pp. 327-332, Apr. 2002.*
Alden et al., "In vivo endochondral bone formation using a bone morphogenetic protein 2 adenoviral vector," Hum. Gene Ther., vol. 10, pp. 2245-2253 (1999).
Arts et al., "Adenoviral Vectors Expressing siRNAs for Discovery and Validation of Gene Function," Genome Res., vol. 13, pp. 2325-2332 (2003).
Bandyopadhyay et al., "Activation of protein kinase C ($\alpha$, $\beta$, and $\zeta$) by insulin in 3T3/L1 cells. Transfection studies suggest a role for PKC-$\zeta$ in glucose transport," J. Biol. Chem., vol. 272, pp. 2551-2558 (1997).
Bass, "RNA Interference. The Short Answer," Nature, vol. 411, No. 6836, pp. 428-429 (May 2001).

(Continued)

*Primary Examiner*—Christopher S. F. Low
*Assistant Examiner*—Jennifer Dunston
(74) *Attorney, Agent, or Firm*—Fitzpatrick, Cella, Harper & Scinto

(57) ABSTRACT

The present invention is based on the discovery that $\zeta$PKC expression is increased in the tissues of arthritis patients as compared to normal individuals. Accordingly, the present invention provides methods of diagnosing, prognosing, and monitoring the course of arthritis in a patient based on increased $\zeta$PKC gene expression in arthritic tissue. The present invention further provides compounds that inhibit the expression of $\zeta$PKC for use as remedies in the treatment of arthritis, including, but not limited to, inhibitory polynucleotides and polypeptides, small molecules, and peptide inhibitors. In addition, the present invention provides pharmaceutical formulations and routes of administration for such remedies, as well as methods for assessing their efficacy.

18 Claims, 13 Drawing Sheets

OTHER PUBLICATIONS

Bond et al., "Inhibition of transcription factor NF-κB reduces matrix metalloproteinase-1, -3 and -9 production by vascular smooth muscle cells," Cardiovasc. Res., vol. 50, pp. 556-565 (2001).

Bond et al., "Nuclear factor κB activity is essential for matrix metalloproteinase-1 and -3 upregulation in rabbit dermal fibroblasts," Biochem. Biophys. Res. Commun., vol. 264, pp. 561-567 (1999).

Bond et al., "Synergistic upregulation of metalloproteinase-9 by growth factors and inflammatory cytokines: an absolute requirement for transcription factor NF-κB," FEBS Lett., vol. 435, pp. 29-34 (1998).

Catterall and Cawston, "Drugs in development: bisphosphonates and metalloprotelnase inhibitors," Arthritis. Res. Ther., vol. 5, pp. 12-24 (2003).

Dang et al., "Protein kinase C ζ phosphorylates a subset of selective sites of the NADPH oxidase component p47phox and participates in formyl peptide-mediated neutrophil respiratory burst," J. Immunol., vol. 166, pp. 1206-1213 (2001).

Diaz-Meco et al., "The product of par-4, a gene induced during apoptosis, interacts selectively with the atypical isoforms of protein kinase C," Cell, vol. 86, pp. 777-786 (1996).

Dorn et al., "siRNA relieves chronic neuropathic pain," Nucleic Acids Res., vol. 32 (5), p. e49 (2004).

Elbashir et al., "Duplexes of 21-Nucleotide RNAs Mediate RNA Interference in Cultured Mammalian Cells," Nature, vol. 411, pp. 494-498 (May 2001).

Elbashir et al., "Functional Anatomy of siRNAs for Mediating Efficient RNAi in *Drosophila melanogaster* Embryo Lysate," EMBO J., vol. 20(23), pp. 6877-6888 (Dec. 2001).

Finger et al., "Molecular phenotyping of human chondrocyte cell lines T/C-28a2, T/C-28a4, and C-28/I2," Arthititis Rheum., vol. 48, pp. 3395-3403 (2003).

Galderisi et al., "Antisense Oligonucleotides as Therapeutic Agents," J. Cell Physiol., vol. 181(2), pp. 251-257 (Nov. 1999).

Goekjian and Jirousek, "Protein kinase C inhibitors as novel anticancer drugs," Expert. Opin. Investig. Drugs, vol. 10, pp. 2117-2140 (2001).

Heasman, "Morpholino Oligos: Making Sense of Antisense?," Develop. Biol., vol. 243(2), pp. 209-214 (Mar. 2002).

Herbert et al., "Chelerythrine is a potent and specific inhibitor of protein kinase C," Biochem. Biophys. Res. Commun., vol. 172, pp. 993-999 (1990).

Herget et al., "The myristoylated alanine-rich C-kinase substrate (MARCKS) is sequentially phosphorylated by conventional, novel and atypical isotypes of protein kinase C," Eur. J. Biochem., vol. 233, pp. 448-457 (1995).

Hill et al. "Genomic Analysis of Gene Expression in *C. elegans*", Science, vol. 290, pp. 809-812 (Oct. 2000).

Hussain et al., "Activation of Protein Kinase C ζ Is Essential for Cytokine-induced Metalloproteinase-1, -3, and -9 Secretion from Rabbit Smooth Muscle Cells and Inhibits Proliferation," J. Biol. Chem., vol. 277, pp. 27345-27352 (2002).

Jordan et al., "Differential Effects of Protein Kinase C Inhibitors on Chemokine Production in Human Synovial Fibroblasts," Br. J. Pharmacol., vol. 117, pp. 1245-1253 (1996).

Kim et al., "p38 kinase-dependent and -Independent inhibition of protein kinase C ζ and α regulates nitric oxide-induced apoptosis and dedifferentiation of articular chondrocytes," J. Biol. Chem., vol. 277, pp. 30375-30381 (2002).

Knauert and Glazer, "Triplex Forming Oligonucleotides: Sequence-Specific Tools for Gene Targeting," Hum. Mol. Genet., vol. 10(20), pp. 2243-2251 (2001).

Kochs et al., "Activation and substrate specificity of the human protein kinase C alpha and ζ isoenzymes," Eur. J. Biochem., vol. 216(2), pp. 597-606 (1993).

Lallena et al., "Activation of IκB kinase beta by protein kinase C isoforms," Mol. Cell. Biol., vol. 19(3), pp. 2180-2188 (1999).

Leitges et al., "Targeted disruption of the ζ PKC gene results in the impairment of the NF-κB pathway," Mol. Cell, vol. 8, pp. 771-780 (2001).

Lin et al., "Inhibition of nuclear translocation of transcription factor NF-κB by a synthetic peptide containing a cell membrane-permeable motif and nuclear localization sequence," J. Biol. Chem., vol. 270, pp. 14255-14258 (1995).

McGlynn et al., "Expression and partial characterization of rat protein kinase C-delta and protein kinase C-ζ in insect cells using recombinant baculovirus," J. Cell. Biochem., vol. 49, pp. 239-250 (1992).

Micklefield, "Backbone Modification of Nucleic Acids: Synthesis, Structure and Therapeutic Applications," Curr. Med. Chem., vol. 8(10), pp. 1157-1179 (Aug. 2001).

Mort and Billington, "Articular cartilage and changes in arthritis: matrix degradation," Arthritis. Res., vol. 3, pp. 337-341 (2001).

Municio et al., "Identification of heterogeneous ribonucleoprotein A1 as a novel substrate for protein kinase C ζ," J. Biol. Chem., vol. 270, pp. 15884-15891 (1995).

Paddison et al., "Stable Suppression of Gene Expression by RNAi in Mammalian Cells," Proc. Natl. Acad. Sci. USA, vol. 99(3), pp. 1443-1448 (Feb. 2002).

Reynolds et al., "Rational siRNA design for RNA interference," Nat. Biotechnol., vol. 22, pp. 326-330 (2004).

Roshak et al., "Small-molecule inhibitors of NF-κB for the treatment of inflammatory joint disease," Curr. Opin. Pharmacol., vol. 2, pp. 316-321 (2002).

Sioud, "Nucleic Acid Enzymes as a Novel Generation of Anti-Gene Agents," Curr. Mol. Med., vol. 1(5), pp. 575-588 (Nov. 2001).

Smith, "Degradative enzymes in osteoarthritis," Front. Biosci., vol. 4, p. d704-12 (Oct. 1999).

Song et al., "RNA Interference Targeting Fas Protects Mice from Fulminant Hepatitis," Nat. Med., vol. 9(3), pp. 347-351 (Mar. 2003).

Standaert et al., "Okadaic acid activates atypical protein kinase C (ζ/lambda) in rat and 3T3/L1 adipocytes. An apparent requirement for activation of Glut4 translocation and glucose transport," J. Biol. Chem., vol. 274, pp. 14074-14078 (1999).

Sui et al., "A DNA Vector-Based RNAi Technology to Suppress Gene Expression in Mammalian Cells," Proc. Natl. Acad. Sci. USA, vol. 99(8), pp. 5515-5520 (Apr. 2002).

Way et al., "Identification of PKC-isoform-specific biological actions using pharmacological approaches," Trends Pharmacol. Sci., vol. 21, pp. 181-187 (2000).

Xu et al., "Effects of growth factors and interleukin-1 alpha on proteoglycan and type II collagen turnover in bovine nasal and articular chondrocyte pellet cultures," Endocrinology, vol. 137, pp. 3557-3565 (1996).

Yu et al., "RNA Interference by Expression of Short-Interfering RNAs and Hairpin RNAs in Mammalian Cells," Proc. Natl. Acad. Sci. USA, vol. 99(9), pp. 6047-6052 (Apr. 2002).

Zhou et al., "Nucleolin is a protein kinase C-ζ substrate. Connection between cell surface signaling and nucleus in PC12 cells," J. Biol. Chem., vol. 272, pp. 31130-31137 (1997).

Voet & Voet, *Biochemistry*, p. 14 ($2^{nd}$ Ed. 1995).

Alexis "10Z-Hymenialdisine" Product Data Sheet, available at:www.alexis-corp.com, 2 pgs., printed on May 27, 2005.

EMD "Hymenialdisine" Product Sheet, available at: www.embiosciences.com, 2 pgs., printed on May 27, 2005.

Wan et al. "Synthesis and Target identification of Hymenialdisine Analogs," Chem. Biol. 11:247-59 (2004).

Inoue et al. "An investigation of cell proliferation and soluble mediators induced by interleukin 1 β in human synovial fibroblasts: comparative response in osteoarthritis and rheumatoid arthritis," Inflamm. Res. 50:65-72 (2001).

Freed et al. "In Vitro Modulation of Chondrogenesis," Clin. Ortho. Related Res. 367S:S46-S58 (1999).

Lübke et al. "Growth characterization of neo porcine cartilage pellets and their use in an interactive culture model," Osteoarthr. Cartilage 13:478-87 (2005).

Ermis et al. "Invasion of Human Cartilage by Cultured Multicellular Spheroids of Rheumatoid Synovial Cells—A Novel in Vitro Model System for Rheumatoid Arthritis," J. Rheum. 25: 208-13 (1998).

Guicheux et al. "A Novel In Vitro Culture System for Analysis of Functional role of Phosphate Transport in Endochondral Ossification," Bone 27:69-74 (2000).

Smith et al. "Characterization of a Human Colorectal Carcinoma Cell Line with Acquired Resistance to Flavopiridol," Mol. Pharmacol. 60:885-93 (2001).

Biernat et al. "Protein Kinase MARK/PAR-1 Is Required for Neurite Outgrowth and Establishment of Neuronal Polarity," Mol. Biol. Cell 13:4013-28 (2002).

Breton and Chabot-Fletcher "The Natural Product Hymenialdisine Inhibits Interleukin-8 Production in U937 Cells by Inhibition of Nuclear Factor$_R$B," J. Pharm. Exp. Ther. 282:459-66 (1997).

Carlson and Longaker "The fibroblast-populated collagen matrix as a model of wound healing : a review of the evidence," Wound Rep. Reg. 12:134-47 (2004).

Bates et al. "Spheroids and cell survival," Crit. Rev. Oncol. Hematol. 36:61-74 (2000).

Kim et al. "Three-dimensional in vitro tissue culture models of breast cancer—a review," Breast Cancer Res. Treat.. 149:1-11 (2004).

Moritani et al. "Comparable response of ccn1 with ccn2 genes upon arthritis: An in vitro evaluation with a human chondrocytic cell line stimulated by a set of cytokines," Cell Comm. Signal 3:6 (8 pgs.).

Reinholz et al. "Animal models for cartilage reconstruction," Biomaterials 25:1511-21 (2004).

Mello et al. "High Density Micromass Cultures of Embryonic Limb Bud Mesenchymal Cells: an In Vitro Model of Endochondral Skeletal Development," In Vitro Cell. Dev. Biol.—Animal 35:262-69 (1999).

Karp, Peter D. "An ontology for biological function based on molecular interactions," Bioinfo. Ontol. 16:269-85 (2000).

Verkman, A.S. "Drug discovery in academia," Am. J. Physiol. Cell 286:465-74 (2004).

Haas et al. "Murine C3H10T1/2 Multipotential Cells as an In Vitro Model of Mesenchymal Chondrogenesis" in Meth. Mol. Biol. (vol. 137:Dev. Bio. Protocols, vol. 3) 383-89 Tuan & Lo (Eds.) Humana Press Inc., Totowa, N.J.

DeLise et al. "Embryonic Limb Mesenchyme Micromass Culture as an In Vitro Model for Chondrogenesis and Cartilage Maturation" in Meth. Mol. Biol. (vol. 137:Dev. Bio. Protocols, vol. 3) 359-75 Tuan & Lo (Eds.) Humana Press Inc., Totowa, N.J.

Neidhart et al. "Anti-Interleukin-1 and Anti-CD44 Interventions Producing Significant Inhibition of cartilage Destruction in an In Vitro Model of Cartilage Invasion by Rheumatoid Arthritis Synovial Fibroblasts," Arth. Rheum. 43:1719-28 (2000).

Whitter et al. "The Immunologic Detection and Characterization of Cartilage Proteoglycan Degradation Products in Synovial fluids of Patients with Arthritis," Arth. Rheum. 30:519-29 (1987).

Ono et al. "Protein kinase C$\zeta$ subspecies from rat brain: its structure, expression and properties," Proc. Natl. Acad. Sci. USA, 86:3099-103 (1989).

Ring and Cohen "Modeling protein structures: construction and their applications," FASEB J. 7:783-90 (1993).

Pieper et al. "MODBASE, a database of annotated comparative protein structure models, and associated resources," Nucl. Acids Res. 32:D217-D222 (2004).

Meijer et al. "Inhibition of cyclin-dependent kinases, GSK-$\beta$ and CK1 by hymenialdisine, a marine sponge constituent," Chem. Biol. 17:51-63 (2000).

Sandell et al. "Article cartilage and changes in arthritis An introduction: Cell biology of osteoarthritis," Arth. Res. 3:107-13 (2001).

Bendele (2001) "Animal Models of Osteoarthritis," J. Musculoskel. Neuron Interact. 1:363-76.

Griffiths and Schrier (2003) "Advantages and Limitations of Animal Models in the Discovery and Evaluation of Novel Disease Modifying Osteoarthritis Drugs (DMOADs)" in *Osteoarthritis*, Eds. Brandt et al., Oxford University Press, Oxford, England, Ch 11.3, p. 411-16.

Brandt (2002) "Animal Models of Osteoarthritis," Biorheology 39:221-35.

Biomol "Hymenialdisine," Product Data Sheet, available at: www.biomol.com, 2 pp. (Print date: Jun. 19, 2006).

Pap et al. (2000) "Fibroblast Biology: Role of Synovial Fibroblasts in the Pathogenesis of Rheumatoid Arthritis," Arthritis Res. 2:361-67.

Goldring (2000) "Osteoarthritis and Cartilage: The Role of Cytokines" Curr. Rheum. Reports 2:459-465 [Exhibit 2 of concurrently filed 37 C.F.R. §1.132 Declaration].

Martel-Pelletier (1999) "Pathophysiology of Osteoarthritis" Osteo. Cart. 7:371-73.

Glasson et al. (2005) "Deletion of Active ADAMTS5 Prevents Cartilage Degradation in a Murine Model of Osteoarthritis," Nature 434:644-648.

Glasson (2007) "In Vivo Osteoarthritis Target Validation Utilizing Genetically Modified Mice," Curr. Drug Targets 8:367-76.

Janusz et al. (2002) "Induction of Osteoarthritis in the Rat by Surgical Tear of The Meniscus: Inhibition of Joint Damage by a Matrix Metalloproteinase Inhibitor," Osteo. Cartilage 10:785-91.

Kerr L. D. (2003) "Inflammatory Arthritis in The Elderly," Mt. Sinai J. Med. 70:23-26.

Malfait et al. (2002) "Inhibition of ADAM-TS4 and ADAM-TS5 Prevents Aggrecan Degradation in Osteoarthritic Cartilage," J. Biol. Chem. 277:22201-208 [Exhibit 4 of concurrently filed 37 C.F.R. §1.132 Declaration].

Struglics et al. (2006) "Human Osteoarthritis Synovial Fluid and Joint Cartilage Contain Both Aggrecanase- and Matrix Metalloproteinase-Generated Aggrecan Fragments," Osteo. Cartilage 14:101-13 [Exhibit 5 of concurrently filed 37 C.F.R. §1.132 Declaration].

PKC Inhibitor Table, available at http://www.pkclab.org/PKC/PKCbiology_PKC_inhibitors.htm, 15 pp. (Print date: Apr. 10, 2007).

Zhang et al. (2004) "Hyaline Cartilage Engineered by chondrocytes in Pellet Culture: Histological, Immunological and Ultrastructural Analysis in Comparison with Cartilage Explants," J. Anat. 2005:229-37 [Exhibit 3 of concurrently filed 37 C.F.R. §1.132 Declaration].

Goldring and Goldring (2007) "Osteoarthritis" *J. Cell Physiol.* 213:626-34.

Goldring (2000) "The role of the chondrocyte in osteoarthritis" *Arthritis & Rheumatism* 43:1916-26.

Goldring (2006) "Update on the biology of the chondrocyte and new approaches to treating cartilage diseases" *Best Practice & Research Clinical Rheumatology* 20:1003-25.

Monaco et al. (2004) "T-Cell-Mediated Signalling in Immune, Inflammatory and Angiogenic Processes: The Cascade of Events Leading to Inflammatory Diseases" *Current Drug Targets—Inflammation & Allergy* 3:35-42.

Krane and Goldring (1990) "Clinical Implications of Cartilage Metabolism in Arthritis" *Eur. J. Rheumatol. Inflamm.* 10:4-9.

Verbruggen (2006) "Chondroprotective drugs in degenerative joint diseases" *Rheumatology* 45:129-38.

Lequesne et al. (2002) "Structural Effect of Avocado/Soybean Unsaponifiables on Joint Space Loss in Osteoarthritis of the Hip" *Arthr. Rheum.* 47:50-58.

Corbit et al. (2000) "Different Protein Kinase C Isoforms Determine Growth Factor Specificity in Neuronal Cells" *Mol. Cell. Biol.* 20:5392-403.

Siomboing et al. (2001) "Investigation of the inhibitory effects of chelerythrine chloride on the translocation of the protein kinase C $\beta$I, $\beta$II, $\zeta$ in human neutrophils" *II Farmaco* 56:859-65.

\* cited by examiner

Figure 1

Target segment starts with AA

| Target segment: 5' -> 3' | GC Ratio | Position | siRNA Sense strand: 5' -> 3'<br>siRNA Antisense strand: 5' -> 3' |
|---|---|---|---|
| AAGTGAGAGACATGTGTCGTC<br>[SEQ ID NO:9] | 0.48 | 127 | GUGAGAGACAUGUGUCGUCUU<br>[SEQ ID NO:21]<br>GACGACACAUGUCUCUCACUU<br>[SEQ ID NO:33] |
| AAGATGGAGGAAGCTGTACCG<br>[SEQ ID NO:10] | 0.52 | 359 | GAUGGAGGAAGCUGUACCGUU<br>[SEQ ID NO:22]<br>CGGUACAGCUUCCUCCAUCUU<br>[SEQ ID NO:34] |
| AAGGCTACAGGTGCATCAACT<br>[SEQ ID NO:11] | 0.48 | 469 | GGCUACAGGUGCAUCAACUUU<br>[SEQ ID NO:23]<br>AGUUGAUGCACCUGUAGCCUU<br>[SEQ ID NO:35] |
| AACTGCTGGTCCATAAGCGCT<br>[SEQ ID NO:12] | 0.52 | 493 | CUGCUGGUCCAUAAGCGCUUU<br>[SEQ ID NO:24]<br>AGCGCUUAUGGACCAGCAGUU<br>[SEQ ID NO:36] |
| AAGAGCCTCCAGTAGACGACA<br>[SEQ ID NO:13] | 0.52 | 571 | GAGCCUCCAGUAGACGACAUU<br>[SEQ ID NO:25]<br>UGUCGUCUACUGGAGGCUCUU<br>[SEQ ID NO:37] |
| AAGACGACTCGGAGGACCTTA<br>[SEQ ID NO:14] | 0.52 | 673 | GACGACUCGGAGGACCUUAUU<br>[SEQ ID NO:26]<br>UAAGGUCCUCCGAGUCGUCUU<br>[SEQ ID NO:38] |
| AAGAGCTGGTGCATGATGACG<br>[SEQ ID NO:15] | 0.52 | 853 | GAGCUGGUGCAUGAUGACGUU<br>[SEQ ID NO:27]<br>CGUCAUCAUGCACCAGCUCUU<br>[SEQ ID NO:39] |
| AAGTCGGTTGTTCCTGGTCAT<br>[SEQ ID NO:16] | 0.48 | 968 | GUCGGUUGUUCCUGGUCAUUU<br>[SEQ ID NO:28]<br>AUGACCAGGAACAACCGACUU<br>[SEQ ID NO:40] |
| AAGCTCACAGACTACGGCATG<br>[SEQ ID NO:17] | 0.52 | 1170 | GCUCACAGACUACGGCAUGUU<br>[SEQ ID NO:29]<br>CAUGCCGUAGUCUGUGAGCUU<br>[SEQ ID NO:41] |

Figure 1 continued

| Target segment: 5' -> 3' | GC Ratio | Position | siRNA Sense strand: 5' -> 3'<br>siRNA Antisense strand: 5' -> 3' |
|---|---|---|---|
| AAGAGGATCGACCAGTCAGAG<br>[SEQ ID NO:18] | 0.52 | 1701 | GAGGAUCGACCAGUCAGAGUU<br>[SEQ ID NO:30]<br>CUCUGACUGGUCGAUCCUCUU<br>[SEQ ID NO:42] |
| AACTGTATCCTTAACCACCGC<br>[SEQ ID NO:19] | 0.48 | 1822 | CUGUAUCCUUAACCACCGCUU<br>[SEQ ID NO:31]<br>GCGGUGGUUAAGGAUACAGUU<br>[SEQ ID NO:43] |
| AACCACCGCATATGCATGCCA<br>[SEQ ID NO:20] | 0.52 | 1834 | CCACCGCAUAUGCAUGCCAUU<br>[SEQ ID NO:32]<br>UGGCAUGCAUAUGCGGUGGUU<br>[SEQ ID NO:44] |

Target segment starts with CA

| Target segment: 5' -> 3' | GC Ratio | Position | siRNA Sense strand: 5' -> 3'<br>siRNA Antisense strand: 5' -> 3' |
|---|---|---|---|
| CAGAAGATGGAGGAAGCTGTA<br>[SEQ ID NO:45] | 0.48 | 356 | GAAGAUGGAGGAAGCUGUAUU<br>[SEQ ID NO:60]<br>UACAGCUUCCUCCAUCUUCUU<br>[SEQ ID NO:75] |
| CAAGGCTACAGGTGCATCAAC<br>[SEQ ID NO:46] | 0.52 | 468 | AGGCUACAGGUGCAUCAACUU<br>[SEQ ID NO:61]<br>GUUGAUGCACCUGUAGCCUUU<br>[SEQ ID NO:76] |
| CAGTAGACGACAAGAACGAGG<br>[SEQ ID NO:47] | 0.52 | 580 | GUAGACGACAAGAACGAGGUU<br>[SEQ ID NO:62]<br>CCUCGUUCUUGUCGUCUACUU<br>[SEQ ID NO:77] |
| CAGACGACAAGTCGGTTGTTC<br>[SEQ ID NO:48] | 0.52 | 960 | GACGACAAGUCGGUUGUUCUU<br>[SEQ ID NO:63]<br>GAACAACCGACUUGUCGUCUU<br>[SEQ ID NO:78] |
| CAAGTCGGTTGTTCCTGGTCA<br>[SEQ ID NO:49] | 0.52 | 967 | AGUCGGUUGUUCCUGGUCAUU<br>[SEQ ID NO:64]<br>UGACCAGGAACAACCGACUUU<br>[SEQ ID NO:79] |
| CACATCAAGCTCACAGACTAC<br>[SEQ ID NO:50] | 0.48 | 1164 | CAUCAAGCUCACAGACUACUU<br>[SEQ ID NO:65]<br>GUAGUCUGUGAGCUUGAUGUU<br>[SEQ ID NO:80] |

Figure 1 continued

| | | | |
|---|---|---|---|
| CATCAAGCTCACAGACTACGG [SEQ ID NO:51] | 0.52 | 1166 | UCAAGCUCACAGACUACGGUU [SEQ ID NO:66] <br> CCGUAGUCUGUGAGCUUGAUU [SEQ ID NO:81] |
| CAAGCTCACAGACTACGGCAT [SEQ ID NO:52] | 0.52 | 1169 | AGCUCACAGACUACGGCAUUU [SEQ ID NO:67] <br> AUGCCGUAGUCUGUGAGCUUU [SEQ ID NO:82] |
| CACAGACTACGGCATGTGCAA [SEQ ID NO:53] | 0.52 | 1175 | CAGACUACGGCAUGUGCAAUU [SEQ ID NO:68] <br> UUGCACAUGCCGUAGUCUGUU [SEQ ID NO:83] |
| CATGAACACAGAGGACTACCT [SEQ ID NO:54] | 0.48 | 1376 | UGAACACAGAGGACUACCUUU [SEQ ID NO:69] <br> AGGUAGUCCUCUGUGUUCAUU [SEQ ID NO:84] |
| CATTCCAGCCACAGATCACAG [SEQ ID NO:55] | 0.52 | 1600 | UUCCAGCCACAGAUCACAGUU [SEQ ID NO:70] <br> CUGUGAUCUGUGGCUGGAAUU [SEQ ID NO:85] |
| CACAGATCACAGACGACTACG [SEQ ID NO:56] | 0.52 | 1609 | CAGAUCACAGACGACUACGUU [SEQ ID NO:71] <br> CGUAGUCGUCUGUGAUCUGUU [SEQ ID NO:86] |
| CAGATCACAGACGACTACGGT [SEQ ID NO:57] | 0.52 | 1611 | GAUCACAGACGACUACGGUUU [SEQ ID NO:72] <br> ACCGUAGUCGUCUGUGAUCUU [SEQ ID NO:87] |
| CAGACGATGAGGATGCCATAA [SEQ ID NO:58] | 0.48 | 1681 | GACGAUGAGGAUGCCAUAAUU [SEQ ID NO:73] <br> UUAUGGCAUCCUCAUCGUCUU [SEQ ID NO:88] |
| CATTATTGCTGTCCACCGAGG [SEQ ID NO:59] | 0.52 | 1747 | UUAUUGCUGUCCACCGAGGUU [SEQ ID NO:74] <br> CCUCGGUGGACAGCAAUAAUU [SEQ ID NO:89] |

Figure 1 continued

Target segment starts with GA

| Target segment: 5' -> 3' | GC Ratio | Position | siRNA Sense strand: 5' -> 3'<br>siRNA Antisense strand: 5' -> 3' |
|---|---|---|---|
| GAGCTCTGTGAGGAAGTGAGA<br>[SEQ ID NO:90] | 0.52 | 114 | GCUCUGUGAGGAAGUGAGAUU<br>[SEQ ID NO:110]<br>UCUCACUUCCUCACAGAGCUU<br>[SEQ ID NO:130] |
| GAGGAAGTGAGAGACATGTGT<br>[SEQ ID NO:91] | 0.48 | 123 | GGAAGUGAGAGACAUGUGUUU<br>[SEQ ID NO:111]<br>ACACAUGUCUCUCACUUCCUU<br>[SEQ ID NO:131] |
| GAAGTGAGAGACATGTGTCGT<br>[SEQ ID NO:92] | 0.48 | 126 | AGUGAGAGACAUGUGUCGUUU<br>[SEQ ID NO:112]<br>ACGACACAUGUCUCUCACUUU<br>[SEQ ID NO:132] |
| GAGAGACATGTGTCGTCTGCA<br>[SEQ ID NO:93] | 0.52 | 131 | GAGACAUGUGUCGUCUGCAUU<br>[SEQ ID NO:113]<br>UGCAGACGACACAUGUCUCUU<br>[SEQ ID NO:133] |
| GAAGATGGAGGAAGCTGTACC<br>[SEQ ID NO:94] | 0.52 | 358 | AGAUGGAGGAAGCUGUACCUU<br>[SEQ ID NO:114]<br>GGUACAGCUUCCUCCAUCUUU<br>[SEQ ID NO:134] |
| GACCTGCAGGAAGCATATGGA<br>[SEQ ID NO:95] | 0.52 | 533 | CCUGCAGGAAGCAUAUGGAUU<br>[SEQ ID NO:115]<br>UCCAUAUGCUUCCUGCAGGUU<br>[SEQ ID NO:135] |
| GAGGAGACAGATGGAATTGCT<br>[SEQ ID NO:96] | 0.48 | 618 | GGAGACAGAUGGAAUUGCUUU<br>[SEQ ID NO:116]<br>AGCAAUUCCAUCUGUCUCCUU<br>[SEQ ID NO:136] |
| GAGGACCTTAAGCCAGTTATC<br>[SEQ ID NO:97] | 0.48 | 684 | GGACCUUAAGCCAGUUAUCUU<br>[SEQ ID NO:117]<br>GAUAACUGGCUUAAGGUCCUU<br>[SEQ ID NO:137] |
| GATGACGAGGATATTGACTGG<br>[SEQ ID NO:98] | 0.48 | 867 | UGACGAGGAUAUUGACUGGUU<br>[SEQ ID NO:118]<br>CCAGUCAAUAUCCUCGUCAUU<br>[SEQ ID NO:138] |

Figure 1 continued

| | | | |
|---|---|---|---|
| GATTACACTCCTGCTTCCAGA [SEQ ID NO:99] | 0.48 | 943 | UUACACUCCUGCUUCCAGAUU [SEQ ID NO:119]<br>UCUGGAAGCAGGAGUGUAAUU [SEQ ID NO:139] |
| GACGACAAGTCGGTTGTTCCT [SEQ ID NO:100] | 0.52 | 962 | CGACAAGUCGGUUGUUCCUUU [SEQ ID NO:120]<br>AGGAACAACCGACUUGUCGUU [SEQ ID NO:140] |
| GACAAGTCGGTTGTTCCTGGT [SEQ ID NO:101] | 0.52 | 965 | CAAGUCGGUUGUUCCUGGUUU [SEQ ID NO:121]<br>ACCAGGAACAACCGACUUGUU [SEQ ID NO:141] |
| GACCTGATGTTCCACATGCAG [SEQ ID NO:102] | 0.52 | 1008 | CCUGAUGUUCCACAUGCAGUU [SEQ ID NO:122]<br>CUGCAUGUGGAACAUCAGGUU [SEQ ID NO:142] |
| GATGTTCCACATGCAGAGGCA [SEQ ID NO:103] | 0.52 | 1013 | UGUUCCACAUGCAGAGGCAUU [SEQ ID NO:123]<br>UGCCUCUGCAUGUGGAACAUU [SEQ ID NO:143] |
| GACTACGGCATGTGCAAGGAA [SEQ ID NO:104] | 0.52 | 1179 | CUACGGCAUGUGCAAGGAAUU [SEQ ID NO:124]<br>UUCCUUGCACAUGCCGUAGUU [SEQ ID NO:144] |
| GACATGAACACAGAGGACTAC [SEQ ID NO:105] | 0.48 | 1374 | CAUGAACACAGAGGACUACUU [SEQ ID NO:125]<br>GUAGUCCUCUGUGUUCAUGUU [SEQ ID NO:145] |
| GACTTGCTGGAGAAGAAGCAG [SEQ ID NO:106] | 0.52 | 1569 | CUUGCUGGAGAAGAAGCAGUU [SEQ ID NO:126]<br>CUGCUUCUUCUCCAGCAAGUU [SEQ ID NO:146] |
| GATCACAGACGACTACGGTCT [SEQ ID NO:107] | 0.52 | 1613 | UCACAGACGACUACGGUCUUU [SEQ ID NO:127]<br>AGACCGUAGUCGUCUGUGAUU [SEQ ID NO:147] |
| GAGGATCGACCAGTCAGAGTT [SEQ ID NO:108] | 0.52 | 1703 | GGAUCGACCAGUCAGAGUUUU [SEQ ID NO:128]<br>AACUCUGACUGGUCGAUCCUU [SEQ ID NO:148] |

Figure 1 continued

| Target segment: 5' -> 3' | GC Ratio | Position | siRNA Sense strand: 5' -> 3'<br>siRNA Antisense strand: 5' -> 3' |
|---|---|---|---|
| GATCGACCAGTCAGAGTTCGA<br>[SEQ ID NO:109] | 0.52 | 1706 | UCGACCAGUCAGAGUUCGAUU<br>[SEQ ID NO:129]<br>UCGAACUCUGACUGGUCGAUU<br>[SEQ ID NO:149] |

Target segment starts with TA

| Target segment: 5' -> 3' | GC Ratio | Position | siRNA Sense strand: 5' -> 3'<br>siRNA Antisense strand: 5' -> 3' |
|---|---|---|---|
| TAGACGACAAGAACGAGGACG<br>[SEQ ID NO:150] | 0.52 | 583 | GACGACAAGAACGAGGACGUU<br>[SEQ ID NO:155]<br>CGUCCUCGUUCUUGUCGUCUU<br>[SEQ ID NO:160] |
| TACAGACAGAGAAGCACGTGT<br>[SEQ ID NO:151] | 0.48 | 889 | CAGACAGAGAAGCACGUGUUU<br>[SEQ ID NO:156]<br>ACACGUGCUUCUCUGUCUGUU<br>[SEQ ID NO:161] |
| TACACTCCTGCTTCCAGACGA<br>[SEQ ID NO:152] | 0.52 | 946 | CACUCCUGCUUCCAGACGAUU<br>[SEQ ID NO:157]<br>UCGUCUGGAAGCAGGAGUGUU<br>[SEQ ID NO:162] |
| TATTGCTGTCCACCGAGGAGT<br>[SEQ ID NO:153] | 0.52 | 1750 | UUGCUGUCCACCGAGGAGUUU<br>[SEQ ID NO:158]<br>ACUCCUCGGUGGACAGCAAUU<br>[SEQ ID NO:163] |
| TAACCACCGCATATGCATGCC<br>[SEQ ID NO:154] | 0.52 | 1833 | ACCACCGCAUAUGCAUGCCUU<br>[SEQ ID NO:159]<br>GGCAUGCAUAUGCGGUGGUUU<br>[SEQ ID NO:164] |

Figure 5
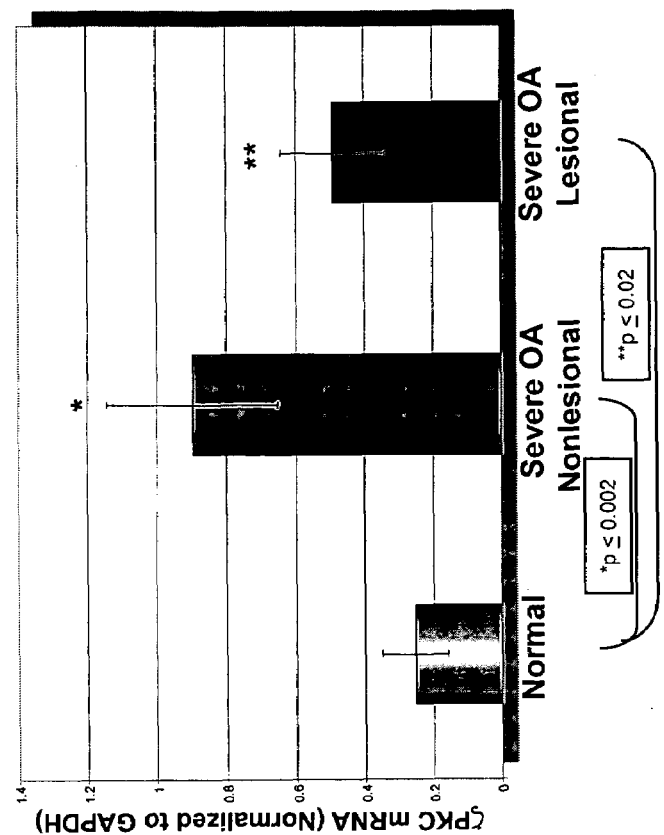
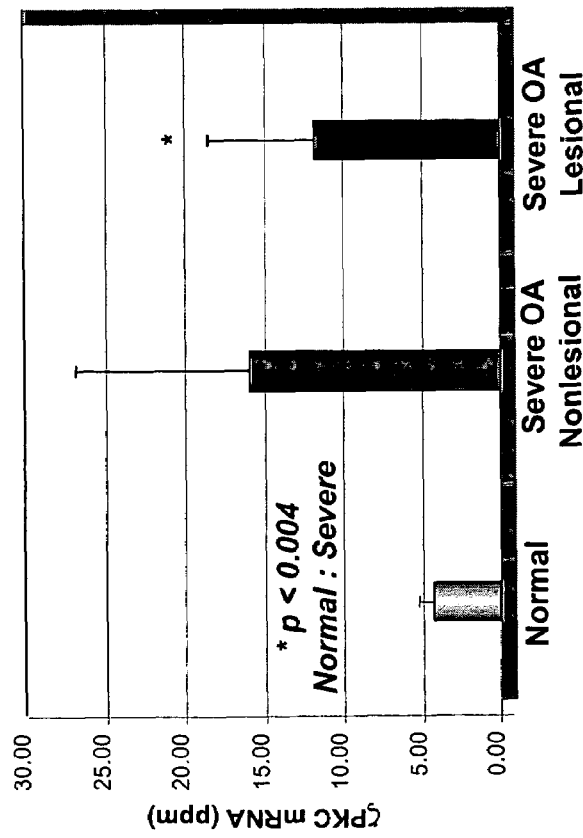

Figure 6
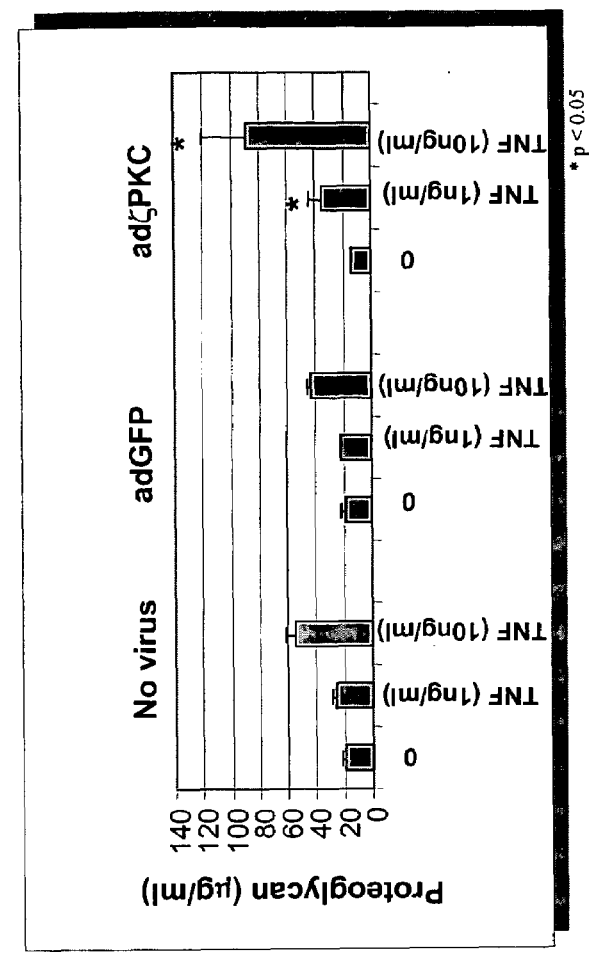
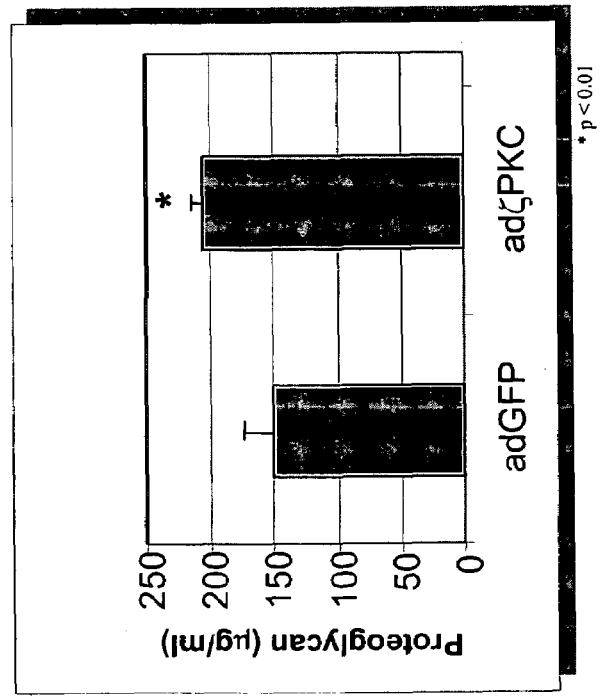

SEQUENCE LISTING

```
<160> NUMBER OF SEQ ID NOS: 164

<210> SEQ ID NO 1
<211> LENGTH: 2164
<212> TYPE: DNA
<213> ORGANISM: Homo sapiens
<220> FEATURE:
```

-continued

```
<221> NAME/KEY: CDS
<222> LOCATION: (1)..(1779)

<400> SEQUENCE: 1
```

| | | | | | | | | | | | | | | | | |
|---|---|---|---|---|---|---|---|---|---|---|---|---|---|---|---|---|
| atg | ccc | agc | agg | acc | gac | ccc | aag | atg | gaa | ggg | agc | ggc | ggc | cgc | gtc | 48 |
| Met | Pro | Ser | Arg | Thr | Asp | Pro | Lys | Met | Glu | Gly | Ser | Gly | Gly | Arg | Val | |
| 1 | | | | 5 | | | | | 10 | | | | | 15 | | |
| cgc | ctc | aag | gcg | cat | tac | ggg | ggg | gac | atc | ttc | atc | acc | agc | gtg | gac | 96 |
| Arg | Leu | Lys | Ala | His | Tyr | Gly | Gly | Asp | Ile | Phe | Ile | Thr | Ser | Val | Asp | |
| | | | 20 | | | | | 25 | | | | | 30 | | | |
| gcc | gcc | acg | acc | ttc | gag | gag | ctc | tgt | gag | gaa | gtg | aga | gac | atg | tgt | 144 |
| Ala | Ala | Thr | Thr | Phe | Glu | Glu | Leu | Cys | Glu | Glu | Val | Arg | Asp | Met | Cys | |
| | | 35 | | | | | 40 | | | | | 45 | | | | |
| cgt | ctg | cac | cag | cag | cac | ccg | ctc | acc | ctc | aag | tgg | gtg | gac | agc | gaa | 192 |
| Arg | Leu | His | Gln | Gln | His | Pro | Leu | Thr | Leu | Lys | Trp | Val | Asp | Ser | Glu | |
| | 50 | | | | | 55 | | | | | 60 | | | | | |
| ggt | gac | cct | tgc | acg | gtg | tcc | tcc | cag | atg | gag | ctg | gaa | gag | gct | ttc | 240 |
| Gly | Asp | Pro | Cys | Thr | Val | Ser | Ser | Gln | Met | Glu | Leu | Glu | Glu | Ala | Phe | |
| 65 | | | | 70 | | | | | 75 | | | | | 80 | | |
| cgc | ctg | gcc | cgt | cag | tgc | agg | gat | gaa | ggc | ctc | atc | att | cat | gtt | ttc | 288 |
| Arg | Leu | Ala | Arg | Gln | Cys | Arg | Asp | Glu | Gly | Leu | Ile | Ile | His | Val | Phe | |
| | | | 85 | | | | | 90 | | | | | 95 | | | |
| ccg | agc | acc | cct | gag | cag | cct | ggc | ctg | cca | tgt | ccg | gga | gaa | gac | aaa | 336 |
| Pro | Ser | Thr | Pro | Glu | Gln | Pro | Gly | Leu | Pro | Cys | Pro | Gly | Glu | Asp | Lys | |
| | | 100 | | | | | 105 | | | | | 110 | | | | |
| tct | atc | tac | cgc | cgg | gga | gcc | aga | aga | tgg | agg | aag | ctg | tac | cgt | gcc | 384 |
| Ser | Ile | Tyr | Arg | Arg | Gly | Ala | Arg | Arg | Trp | Arg | Lys | Leu | Tyr | Arg | Ala | |
| | 115 | | | | | 120 | | | | | 125 | | | | | |
| aac | ggc | cac | ctc | ttc | caa | gcc | aag | cgc | ttt | aac | agg | aga | gcg | tac | tgc | 432 |
| Asn | Gly | His | Leu | Phe | Gln | Ala | Lys | Arg | Phe | Asn | Arg | Arg | Ala | Tyr | Cys | |
| 130 | | | | | 135 | | | | | 140 | | | | | | |
| ggt | cag | tgc | agc | gag | agg | ata | tgg | ggc | ctc | gcg | agg | caa | ggc | tac | agg | 480 |
| Gly | Gln | Cys | Ser | Glu | Arg | Ile | Trp | Gly | Leu | Ala | Arg | Gln | Gly | Tyr | Arg | |
| 145 | | | | 150 | | | | | 155 | | | | | 160 | | |
| tgc | atc | aac | tgc | aaa | ctg | ctg | gtc | cat | aag | cgc | tgc | cac | ggc | ctc | gtc | 528 |
| Cys | Ile | Asn | Cys | Lys | Leu | Leu | Val | His | Lys | Arg | Cys | His | Gly | Leu | Val | |
| | | | 165 | | | | | 170 | | | | | 175 | | | |
| ccg | ctg | acc | tgc | agg | aag | cat | atg | gat | tct | gtc | atg | cct | tcc | caa | gag | 576 |
| Pro | Leu | Thr | Cys | Arg | Lys | His | Met | Asp | Ser | Val | Met | Pro | Ser | Gln | Glu | |
| | | 180 | | | | | 185 | | | | | 190 | | | | |
| cct | cca | gta | gac | gac | aag | aac | gag | gac | gcc | gac | ctt | cct | tcc | gag | gag | 624 |
| Pro | Pro | Val | Asp | Asp | Lys | Asn | Glu | Asp | Ala | Asp | Leu | Pro | Ser | Glu | Glu | |
| | 195 | | | | | 200 | | | | | 205 | | | | | |
| aca | gat | gga | att | gct | tac | att | tcc | tca | tcc | cgg | aag | cat | gac | agc | att | 672 |
| Thr | Asp | Gly | Ile | Ala | Tyr | Ile | Ser | Ser | Ser | Arg | Lys | His | Asp | Ser | Ile | |
| 210 | | | | | 215 | | | | | 220 | | | | | | |
| aaa | gac | gac | tcg | gag | gac | ctt | aag | cca | gtt | atc | gat | ggg | atg | gat | gga | 720 |
| Lys | Asp | Asp | Ser | Glu | Asp | Leu | Lys | Pro | Val | Ile | Asp | Gly | Met | Asp | Gly | |
| 225 | | | | 230 | | | | | 235 | | | | | 240 | | |
| atc | aaa | atc | tct | cag | ggg | ctt | ggg | ctg | cag | gac | ttt | gac | cta | atc | aga | 768 |
| Ile | Lys | Ile | Ser | Gln | Gly | Leu | Gly | Leu | Gln | Asp | Phe | Asp | Leu | Ile | Arg | |
| | | | 245 | | | | | 250 | | | | | 255 | | | |
| gtc | atc | ggg | cgc | ggg | agc | tac | gcc | aag | gtt | ctc | ctg | gtg | cgg | ttg | aag | 816 |
| Val | Ile | Gly | Arg | Gly | Ser | Tyr | Ala | Lys | Val | Leu | Leu | Val | Arg | Leu | Lys | |
| | | 260 | | | | | 265 | | | | | 270 | | | | |
| aag | aat | gac | caa | att | tac | gcc | atg | aaa | gtg | gtg | aag | aaa | gag | ctg | gtg | 864 |
| Lys | Asn | Asp | Gln | Ile | Tyr | Ala | Met | Lys | Val | Val | Lys | Lys | Glu | Leu | Val | |
| | 275 | | | | | 280 | | | | | 285 | | | | | |
| cat | gat | gac | gag | gat | att | gac | tgg | gta | cag | aca | gag | aag | cac | gtg | ttt | 912 |
| His | Asp | Asp | Glu | Asp | Ile | Asp | Trp | Val | Gln | Thr | Glu | Lys | His | Val | Phe | |

```
                290                 295                 300
gag cag gca tcc agc aac ccc ttc ctg gtc gga tta cac tcc tgc ttc      960
Glu Gln Ala Ser Ser Asn Pro Phe Leu Val Gly Leu His Ser Cys Phe
305                 310                 315                 320 cag acg aca agt cgg ttg ttc ctg gtc att gag tac gtc aac ggc ggg     1008
Gln Thr Thr Ser Arg Leu Phe Leu Val Ile Glu Tyr Val Asn Gly Gly
                325                 330                 335 gac ctg atg ttc cac atg cag agg cag agg aag ctc cct gag gag cac     1056
Asp Leu Met Phe His Met Gln Arg Gln Arg Lys Leu Pro Glu Glu His
            340                 345                 350 gcc agg ttc tac gcg gcc gag atc tgc atc gcc ctc aac ttc ctg cac     1104
Ala Arg Phe Tyr Ala Ala Glu Ile Cys Ile Ala Leu Asn Phe Leu His
        355                 360                 365 gag agg ggg atc atc tac agg gac ctg aag ctg gac aac gtc ctc ctg     1152
Glu Arg Gly Ile Ile Tyr Arg Asp Leu Lys Leu Asp Asn Val Leu Leu
    370                 375                 380 gat gcg gac ggg cac atc aag ctc aca gac tac ggc atg tgc aag gaa     1200
Asp Ala Asp Gly His Ile Lys Leu Thr Asp Tyr Gly Met Cys Lys Glu
385                 390                 395                 400 ggc ctg ggc cct ggt gac aca acg agc act ttc tgc gga acc ccg aat     1248
Gly Leu Gly Pro Gly Asp Thr Thr Ser Thr Phe Cys Gly Thr Pro Asn
                405                 410                 415 tac atc gcc ccc gaa atc ctg cgg gga gag gag tac ggg ttc agc gtg     1296
Tyr Ile Ala Pro Glu Ile Leu Arg Gly Glu Glu Tyr Gly Phe Ser Val
            420                 425                 430 gac tgg tgg gcg ctg gga gtc ctc atg ttt gag atg atg gcc ggg cgc     1344
Asp Trp Trp Ala Leu Gly Val Leu Met Phe Glu Met Met Ala Gly Arg
        435                 440                 445 tcc ccg ttc gac atc atc acc gac aac ccg gac atg aac aca gag gac     1392
Ser Pro Phe Asp Ile Ile Thr Asp Asn Pro Asp Met Asn Thr Glu Asp
    450                 455                 460 tac ctt ttc caa gtg atc ctg gag aag ccc atc cgg atc ccc cgg ttc     1440
Tyr Leu Phe Gln Val Ile Leu Glu Lys Pro Ile Arg Ile Pro Arg Phe
465                 470                 475                 480 ctg tcc gtc aaa gcc tcc cat gtt tta aaa gga ttt tta aat aag gac     1488
Leu Ser Val Lys Ala Ser His Val Leu Lys Gly Phe Leu Asn Lys Asp
                485                 490                 495 ccc aaa gag agg ctc ggc tgc cgg cca cag act gga ttt tct gac atc     1536
Pro Lys Glu Arg Leu Gly Cys Arg Pro Gln Thr Gly Phe Ser Asp Ile
            500                 505                 510 aag tcc cac gcg ttc ttc cgc agc ata gac tgg gac ttg ctg gag aag     1584
Lys Ser His Ala Phe Phe Arg Ser Ile Asp Trp Asp Leu Leu Glu Lys
        515                 520                 525 aag cag gcg ctc cct cca ttc cag cca cag atc aca gac gac tac ggt     1632
Lys Gln Ala Leu Pro Pro Phe Gln Pro Gln Ile Thr Asp Asp Tyr Gly
    530                 535                 540 ctg gac aac ttt gac aca cag ttc acc agc gag ccc gtg cag ctg acc     1680
Leu Asp Asn Phe Asp Thr Gln Phe Thr Ser Glu Pro Val Gln Leu Thr
545                 550                 555                 560 cca gac gat gag gat gcc ata aag agg atc gac cag tca gag ttc gaa     1728
Pro Asp Asp Glu Asp Ala Ile Lys Arg Ile Asp Gln Ser Glu Phe Glu
                565                 570                 575 ggc ttt gag tat atc aac cca tta ttg ctg tcc acc gag gag tcg gtg     1776
Gly Phe Glu Tyr Ile Asn Pro Leu Leu Leu Ser Thr Glu Glu Ser Val
            580                 585                 590 tga ggccgcgtgc gtctctgtcg tggacacgcg tgattgaccc tttaactgta          1829
tccttaacca ccgcatatgc atgccaggct gggcacggct ccgagggcgg ccagggacag   1889
acgcttgcgc cgagaccgca gagggaagcg tcagcgggcg ctgctgggag cagaacagtc   1949
```

```
cctcacacct ggcccggcag gcagcttcgt gctggaggaa cttgctgctg tgcctgcgtc    2009
gcggcggatc cgcggggacc ctgccgaggg ggctgtcatg cggtttccaa ggtgcacatt    2069
ttccacggaa acagaactcg atgcactgac ctgctccgcc aggaaagtga gcgtgtagcg    2129
tcctgaggaa taaaatgttc cgatgaaaaa aaaaa                               2164
```

<210> SEQ ID NO 2
<211> LENGTH: 592
<212> TYPE: PRT
<213> ORGANISM: Homo sapiens

<400> SEQUENCE: 2

```
Met Pro Ser Arg Thr Asp Pro Lys Met Glu Gly Ser Gly Gly Arg Val
1               5                   10                  15

Arg Leu Lys Ala His Tyr Gly Gly Asp Ile Phe Ile Thr Ser Val Asp
                20                  25                  30

Ala Ala Thr Thr Phe Glu Glu Leu Cys Glu Glu Val Arg Asp Met Cys
            35                  40                  45

Arg Leu His Gln Gln His Pro Leu Thr Leu Lys Trp Val Asp Ser Glu
        50                  55                  60

Gly Asp Pro Cys Thr Val Ser Ser Gln Met Glu Leu Glu Glu Ala Phe
65                  70                  75                  80

Arg Leu Ala Arg Gln Cys Arg Asp Glu Gly Leu Ile Ile His Val Phe
                85                  90                  95

Pro Ser Thr Pro Glu Gln Pro Gly Leu Pro Cys Pro Gly Glu Asp Lys
            100                 105                 110

Ser Ile Tyr Arg Arg Gly Ala Arg Arg Trp Arg Lys Leu Tyr Arg Ala
        115                 120                 125

Asn Gly His Leu Phe Gln Ala Lys Arg Phe Asn Arg Arg Ala Tyr Cys
    130                 135                 140

Gly Gln Cys Ser Glu Arg Ile Trp Gly Leu Ala Arg Gln Gly Tyr Arg
145                 150                 155                 160

Cys Ile Asn Cys Lys Leu Leu Val His Lys Arg Cys His Gly Leu Val
                165                 170                 175

Pro Leu Thr Cys Arg Lys His Met Asp Ser Val Met Pro Ser Gln Glu
            180                 185                 190

Pro Pro Val Asp Asp Lys Asn Glu Asp Ala Asp Leu Pro Ser Glu Glu
        195                 200                 205

Thr Asp Gly Ile Ala Tyr Ile Ser Ser Ser Arg Lys His Asp Ser Ile
    210                 215                 220

Lys Asp Asp Ser Glu Asp Leu Lys Pro Val Ile Asp Gly Met Asp Gly
225                 230                 235                 240

Ile Lys Ile Ser Gln Gly Leu Gly Leu Gln Asp Phe Asp Leu Ile Arg
                245                 250                 255

Val Ile Gly Arg Gly Ser Tyr Ala Lys Val Leu Leu Val Arg Leu Lys
            260                 265                 270

Lys Asn Asp Gln Ile Tyr Ala Met Lys Val Val Lys Lys Glu Leu Val
        275                 280                 285

His Asp Asp Glu Asp Ile Asp Trp Val Gln Thr Glu Lys His Val Phe
    290                 295                 300

Glu Gln Ala Ser Ser Asn Pro Phe Leu Val Gly Leu His Ser Cys Phe
305                 310                 315                 320

Gln Thr Thr Ser Arg Leu Phe Leu Val Ile Glu Tyr Val Asn Gly Gly
                325                 330                 335
```

```
Asp Leu Met Phe His Met Gln Arg Gln Arg Lys Leu Pro Glu Glu His
            340                 345                 350

Ala Arg Phe Tyr Ala Ala Glu Ile Cys Ile Ala Leu Asn Phe Leu His
            355                 360                 365

Glu Arg Gly Ile Ile Tyr Arg Asp Leu Lys Leu Asp Asn Val Leu Leu
            370                 375                 380

Asp Ala Asp Gly His Ile Lys Leu Thr Asp Tyr Gly Met Cys Lys Glu
385                 390                 395                 400

Gly Leu Gly Pro Gly Asp Thr Thr Ser Thr Phe Cys Gly Thr Pro Asn
            405                 410                 415

Tyr Ile Ala Pro Glu Ile Leu Arg Gly Glu Glu Tyr Gly Phe Ser Val
            420                 425                 430

Asp Trp Trp Ala Leu Gly Val Leu Met Phe Glu Met Met Ala Gly Arg
            435                 440                 445

Ser Pro Phe Asp Ile Ile Thr Asp Asn Pro Asp Met Asn Thr Glu Asp
            450                 455                 460

Tyr Leu Phe Gln Val Ile Leu Glu Lys Pro Ile Arg Ile Pro Arg Phe
465                 470                 475                 480

Leu Ser Val Lys Ala Ser His Val Leu Lys Gly Phe Leu Asn Lys Asp
            485                 490                 495

Pro Lys Glu Arg Leu Gly Cys Arg Pro Gln Thr Gly Phe Ser Asp Ile
            500                 505                 510

Lys Ser His Ala Phe Phe Arg Ser Ile Asp Trp Asp Leu Leu Glu Lys
            515                 520                 525

Lys Gln Ala Leu Pro Pro Phe Gln Pro Gln Ile Thr Asp Asp Tyr Gly
            530                 535                 540

Leu Asp Asn Phe Asp Thr Gln Phe Thr Ser Glu Pro Val Gln Leu Thr
545                 550                 555                 560

Pro Asp Asp Glu Asp Ala Ile Lys Arg Ile Asp Gln Ser Glu Phe Glu
            565                 570                 575

Gly Phe Glu Tyr Ile Asn Pro Leu Leu Leu Ser Thr Glu Glu Ser Val
            580                 585                 590

<210> SEQ ID NO 3
<211> LENGTH: 13
<212> TYPE: PRT
<213> ORGANISM: Artificial
<220> FEATURE:
<223> OTHER INFORMATION: peptide inhibitor

<400> SEQUENCE: 3

Ser Ile Tyr Arg Arg Gly Ala Arg Arg Trp Arg Lys Leu
1               5                   10

<210> SEQ ID NO 4
<211> LENGTH: 17
<212> TYPE: PRT
<213> ORGANISM: Artificial
<220> FEATURE:
<223> OTHER INFORMATION: peptide inhibitor

<400> SEQUENCE: 4

Ser Ile Tyr Arg Arg Gly Ala Arg Arg Trp Arg Lys Leu Tyr Arg Ala
1               5                   10                  15

Asn

<210> SEQ ID NO 5
```

-continued

```
<211> LENGTH: 9
<212> TYPE: PRT
<213> ORGANISM: Artificial
<220> FEATURE:
<223> OTHER INFORMATION: peptide inhibitor

<400> SEQUENCE: 5

Arg Arg Gly Ala Arg Arg Trp Arg Lys
1               5

<210> SEQ ID NO 6
<211> LENGTH: 13
<212> TYPE: PRT
<213> ORGANISM: Artificial
<220> FEATURE:
<223> OTHER INFORMATION: peptide inhibitor
<220> FEATURE:
<221> NAME/KEY: LIPID
<222> LOCATION: (1)..(1)
<223> OTHER INFORMATION: MYRISTATE

<400> SEQUENCE: 6

Ser Ile Tyr Arg Arg Gly Ala Arg Arg Trp Arg Lys Leu
1               5                   10

<210> SEQ ID NO 7
<211> LENGTH: 17
<212> TYPE: PRT
<213> ORGANISM: Artificial
<220> FEATURE:
<223> OTHER INFORMATION: peptide inhibitor
<220> FEATURE:
<221> NAME/KEY: LIPID
<222> LOCATION: (1)..(1)
<223> OTHER INFORMATION: MYRISTATE

<400> SEQUENCE: 7

Ser Ile Tyr Arg Arg Gly Ala Arg Arg Trp Arg Lys Leu Tyr Arg Ala
1               5                   10                  15
Asn

<210> SEQ ID NO 8
<211> LENGTH: 9
<212> TYPE: PRT
<213> ORGANISM: Artificial
<220> FEATURE:
<223> OTHER INFORMATION: peptide inhibitor
<220> FEATURE:
<221> NAME/KEY: LIPID
<222> LOCATION: (1)..(1)
<223> OTHER INFORMATION: MYRISTATE

<400> SEQUENCE: 8

Arg Arg Gly Ala Arg Arg Trp Arg Lys
1               5

<210> SEQ ID NO 9
<211> LENGTH: 21
<212> TYPE: DNA
<213> ORGANISM: Homo sapiens

<400> SEQUENCE: 9
aagtgagaga catgtgtcgt c                                             21

<210> SEQ ID NO 10
<211> LENGTH: 21
<212> TYPE: DNA
<213> ORGANISM: Homo sapiens
```

<400> SEQUENCE: 10
aagatggagg aagctgtacc g                                              21

<210> SEQ ID NO 11
<211> LENGTH: 21
<212> TYPE: DNA
<213> ORGANISM: Homo sapiens

<400> SEQUENCE: 11
aaggctacag gtgcatcaac t                                              21

<210> SEQ ID NO 12
<211> LENGTH: 21
<212> TYPE: DNA
<213> ORGANISM: Homo sapiens

<400> SEQUENCE: 12
aactgctggt ccataagcgc t                                              21

<210> SEQ ID NO 13
<211> LENGTH: 21
<212> TYPE: DNA
<213> ORGANISM: Homo sapiens

<400> SEQUENCE: 13
aagagcctcc agtagacgac a                                              21

<210> SEQ ID NO 14
<211> LENGTH: 21
<212> TYPE: DNA
<213> ORGANISM: Homo sapiens

<400> SEQUENCE: 14
aagacgactc ggaggacctt a                                              21

<210> SEQ ID NO 15
<211> LENGTH: 21
<212> TYPE: DNA
<213> ORGANISM: Homo sapiens

<400> SEQUENCE: 15
aagagctggt gcatgatgac g                                              21

<210> SEQ ID NO 16
<211> LENGTH: 21
<212> TYPE: DNA
<213> ORGANISM: Homo sapiens

<400> SEQUENCE: 16
aagtcggttg ttcctggtca t                                              21

<210> SEQ ID NO 17
<211> LENGTH: 21
<212> TYPE: DNA
<213> ORGANISM: Homo sapiens

<400> SEQUENCE: 17
aagctcacag actacggcat g                                              21

<210> SEQ ID NO 18
<211> LENGTH: 21
<212> TYPE: DNA

```
<213> ORGANISM: Homo sapiens

<400> SEQUENCE: 18
aagaggatcg accagtcaga g                                              21

<210> SEQ ID NO 19
<211> LENGTH: 21
<212> TYPE: DNA
<213> ORGANISM: Homo sapiens

<400> SEQUENCE: 19
aactgtatcc ttaaccaccg c                                              21

<210> SEQ ID NO 20
<211> LENGTH: 21
<212> TYPE: DNA
<213> ORGANISM: Homo sapiens

<400> SEQUENCE: 20
aaccaccgca tatgcatgcc a                                              21

<210> SEQ ID NO 21
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 21
gugagagaca ugugucgucu u                                              21

<210> SEQ ID NO 22
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 22
gauggaggaa gcuguaccgu u                                              21

<210> SEQ ID NO 23
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 23
ggcuacaggu gcaucaacuu u                                              21

<210> SEQ ID NO 24
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 24
cugcuggucc auaagcgcuu u                                              21

<210> SEQ ID NO 25
<211> LENGTH: 21
<212> TYPE: RNA
<213> ORGANISM: Artificial
```

```
<220> FEATURE:
<223> OTHER INFORMATION: siRNA polynucleotide, synthesized

<400> SEQUENCE: 25
gagccuccag uagacgacau u                                              21

<210> SEQ ID NO 26
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 26
gacgacucgg aggaccuuau u                                              21

<210> SEQ ID NO 27
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 27
gagcuggugc augaugacgu u                                              21

<210> SEQ ID NO 28
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 28
gucgguuguu ccuggucauu u                                              21

<210> SEQ ID NO 29
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 29
gcucacagac uacggcaugu u                                              21

<210> SEQ ID NO 30
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 30
gaggaucgac cagucagagu u                                              21

<210> SEQ ID NO 31
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 31
cuguauccuu aaccaccgcu u                                              21
```

-continued

```
<210> SEQ ID NO 32
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 32
ccaccgcaua ugcaugccau u                                              21

<210> SEQ ID NO 33
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 33
uucacucucu guacacagca g                                              21

<210> SEQ ID NO 34
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 34
uucuaccucc uucgacaugg c                                              21

<210> SEQ ID NO 35
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 35
uuccgauguc cacguaguug a                                              21

<210> SEQ ID NO 36
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 36
uugacgacca gguauucgcg a                                              21

<210> SEQ ID NO 37
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 37
uucucggagg ucaucugcug u                                              21

<210> SEQ ID NO 38
<211> LENGTH: 21
<212> TYPE: RNA
<213> ORGANISM: Artificial
<220> FEATURE:
<223> OTHER INFORMATION: siRNA polynucleotide, synthesized
```

-continued

```
<400> SEQUENCE: 38
uucugcugag ccuccuggaa u                                              21

<210> SEQ ID NO 39
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 39
uucucgacca cguacuacug c                                              21

<210> SEQ ID NO 40
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 40
uucagccaac aaggaccagu a                                              21

<210> SEQ ID NO 41
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 41
uucgaguguc ugaugccgua c                                              21

<210> SEQ ID NO 42
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 42
uucuccuagc uggucagucu c                                              21

<210> SEQ ID NO 43
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 43
uugacauagg aauugguggc g                                              21

<210> SEQ ID NO 44
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 44
uugguggcgu auacguacgg u                                              21

<210> SEQ ID NO 45
```

```
<211> LENGTH: 21
<212> TYPE: DNA
<213> ORGANISM: Homo sapiens

<400> SEQUENCE: 45
cagaagatgg aggaagctgt a                                             21

<210> SEQ ID NO 46
<211> LENGTH: 21
<212> TYPE: DNA
<213> ORGANISM: Homo sapiens

<400> SEQUENCE: 46
caaggctaca ggtgcatcaa c                                             21

<210> SEQ ID NO 47
<211> LENGTH: 21
<212> TYPE: DNA
<213> ORGANISM: Homo sapiens

<400> SEQUENCE: 47
cagtagacga caagaacgag g                                             21

<210> SEQ ID NO 48
<211> LENGTH: 21
<212> TYPE: DNA
<213> ORGANISM: Homo sapiens

<400> SEQUENCE: 48
cagacgacaa gtcggttgtt c                                             21

<210> SEQ ID NO 49
<211> LENGTH: 21
<212> TYPE: DNA
<213> ORGANISM: Homo sapiens

<400> SEQUENCE: 49
caagtcggtt gttcctggtc a                                             21

<210> SEQ ID NO 50
<211> LENGTH: 21
<212> TYPE: DNA
<213> ORGANISM: Homo sapiens

<400> SEQUENCE: 50
cacatcaagc tcacagacta c                                             21

<210> SEQ ID NO 51
<211> LENGTH: 21
<212> TYPE: DNA
<213> ORGANISM: Homo sapiens

<400> SEQUENCE: 51
catcaagctc acagactacg g                                             21

<210> SEQ ID NO 52
<211> LENGTH: 21
<212> TYPE: DNA
<213> ORGANISM: Homo sapiens

<400> SEQUENCE: 52
caagctcaca gactacggca t                                             21
```

<210> SEQ ID NO 53
<211> LENGTH: 21
<212> TYPE: DNA
<213> ORGANISM: Homo sapiens

<400> SEQUENCE: 53
cacagactac ggcatgtgca a                                              21

<210> SEQ ID NO 54
<211> LENGTH: 21
<212> TYPE: DNA
<213> ORGANISM: Homo sapiens

<400> SEQUENCE: 54
catgaacaca gaggactacc t                                              21

<210> SEQ ID NO 55
<211> LENGTH: 21
<212> TYPE: DNA
<213> ORGANISM: Homo sapiens

<400> SEQUENCE: 55
cattccagcc acagatcaca g                                              21

<210> SEQ ID NO 56
<211> LENGTH: 21
<212> TYPE: DNA
<213> ORGANISM: Homo sapiens

<400> SEQUENCE: 56
cacagatcac agacgactac g                                              21

<210> SEQ ID NO 57
<211> LENGTH: 21
<212> TYPE: DNA
<213> ORGANISM: Homo sapiens

<400> SEQUENCE: 57
cagatcacag acgactacgg t                                              21

<210> SEQ ID NO 58
<211> LENGTH: 21
<212> TYPE: DNA
<213> ORGANISM: Homo sapiens

<400> SEQUENCE: 58
cagacgatga ggatgccata a                                              21

<210> SEQ ID NO 59
<211> LENGTH: 21
<212> TYPE: DNA
<213> ORGANISM: Homo sapiens

<400> SEQUENCE: 59
cattattgct gtccaccgag g                                              21

<210> SEQ ID NO 60
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 60
gaagauggag gaagcuguau u            21

```
<210> SEQ ID NO 61
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 61
```
aggcuacagg ugcaucaacu u            21

```
<210> SEQ ID NO 62
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 62
```
guagacgaca agaacgaggu u            21

```
<210> SEQ ID NO 63
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 63
```
gacgacaagu cgguuguucu u            21

```
<210> SEQ ID NO 64
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 64
```
agucgguugu uccuggucau u            21

```
<210> SEQ ID NO 65
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 65
```
caucaagcuc acagacuacu u            21

```
<210> SEQ ID NO 66
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 66
```
ucaagcucac agacuacggu u            21

```
<210> SEQ ID NO 67
<211> LENGTH: 21
<212> TYPE: RNA
<213> ORGANISM: Artificial
```

```
<220> FEATURE:
<223> OTHER INFORMATION: siRNA polynucleotide, synthesized

<400> SEQUENCE: 67
agcucacaga cuacggcauu u                                              21

<210> SEQ ID NO 68
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 68
cagacuacgg caugugcaau u                                              21

<210> SEQ ID NO 69
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 69
ugaacacaga ggacuaccuu u                                              21

<210> SEQ ID NO 70
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 70
uuccagccac agaucacagu u                                              21

<210> SEQ ID NO 71
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 71
cagaucacag acgacuacgu u                                              21

<210> SEQ ID NO 72
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 72
gaucacagac gacuacgguu u                                              21

<210> SEQ ID NO 73
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 73
gacgaugagg augccauaau u                                              21
```

-continued

```
<210> SEQ ID NO 74
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 74
uuauugcugu ccaccgaggu u                                              21

<210> SEQ ID NO 75
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 75
uucuucuacc uccuucgaca u                                              21

<210> SEQ ID NO 76
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 76 uuccgaugu ccacguaguu g                                               21

<210> SEQ ID NO 77
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 77
uucaucugcu guucuugcuc c                                              21

<210> SEQ ID NO 78
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 78
uucugcuguu cagccaacaa g                                              21

<210> SEQ ID NO 79
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 79
uuucagccaa caaggaccag u                                              21

<210> SEQ ID NO 80
<211> LENGTH: 21
<212> TYPE: RNA
<213> ORGANISM: Artificial
<220> FEATURE:
<223> OTHER INFORMATION: siRNA polynucleotide, synthesized
```

```
<400> SEQUENCE: 80
uuguaguucg agugucugau g                                              21

<210> SEQ ID NO 81
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 81
uuaguucgag ugucugaugc c                                              21

<210> SEQ ID NO 82
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 82
uuucgagugu cugaugccgu a                                              21

<210> SEQ ID NO 83
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 83
uugucugaug ccguacacgu u                                              21

<210> SEQ ID NO 84
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 84
uuacuugugu cuccugaugg a                                              21

<210> SEQ ID NO 85
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 85
uuaaggucgg ugucuagugu c                                              21

<210> SEQ ID NO 86
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 86
uugucuagug ucugcugaug c                                              21

<210> SEQ ID NO 87
```

```
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 87
uucuaguguc ugcugaugcc a                                          21

<210> SEQ ID NO 88
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 88
uucugcuacu ccuacgguau u                                          21

<210> SEQ ID NO 89
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 89
uuaauaacga cagguggcuc c                                          21

<210> SEQ ID NO 90
<211> LENGTH: 21
<212> TYPE: DNA
<213> ORGANISM: Homo sapiens

<400> SEQUENCE: 90
gagctctgtg aggaagtgag a                                          21

<210> SEQ ID NO 91
<211> LENGTH: 21
<212> TYPE: DNA
<213> ORGANISM: Homo sapiens

<400> SEQUENCE: 91
gaggaagtga gagacatgtg t                                          21

<210> SEQ ID NO 92
<211> LENGTH: 21
<212> TYPE: DNA
<213> ORGANISM: Homo sapiens

<400> SEQUENCE: 92
gaagtgagag acatgtgtcg t                                          21

<210> SEQ ID NO 93
<211> LENGTH: 21
<212> TYPE: DNA
<213> ORGANISM: Homo sapiens

<400> SEQUENCE: 93
gagagacatg tgtcgtctgc a                                          21

<210> SEQ ID NO 94
<211> LENGTH: 21
<212> TYPE: DNA
<213> ORGANISM: Homo sapiens
```

<400> SEQUENCE: 94
gaagatggag gaagctgtac c                                              21

<210> SEQ ID NO 95
<211> LENGTH: 21
<212> TYPE: DNA
<213> ORGANISM: Homo sapiens

<400> SEQUENCE: 95
gacctgcagg aagcatatgg a                                              21

<210> SEQ ID NO 96
<211> LENGTH: 21
<212> TYPE: DNA
<213> ORGANISM: Homo sapiens

<400> SEQUENCE: 96
gaggagacag atggaattgc t                                              21

<210> SEQ ID NO 97
<211> LENGTH: 21
<212> TYPE: DNA
<213> ORGANISM: Homo sapiens

<400> SEQUENCE: 97
gaggacctta agccagttat c                                              21

<210> SEQ ID NO 98
<211> LENGTH: 21
<212> TYPE: DNA
<213> ORGANISM: Homo sapiens

<400> SEQUENCE: 98
gatgacgagg atattgactg g                                              21

<210> SEQ ID NO 99
<211> LENGTH: 21
<212> TYPE: DNA
<213> ORGANISM: Homo sapiens

<400> SEQUENCE: 99
gattacactc ctgcttccag a                                              21

<210> SEQ ID NO 100
<211> LENGTH: 21
<212> TYPE: DNA
<213> ORGANISM: Homo sapiens

<400> SEQUENCE: 100
gacgacaagt cggttgttcc t                                              21

<210> SEQ ID NO 101
<211> LENGTH: 21
<212> TYPE: DNA
<213> ORGANISM: Homo sapiens

<400> SEQUENCE: 101
gacaagtcgg ttgttcctgg t                                              21

<210> SEQ ID NO 102
<211> LENGTH: 21
<212> TYPE: DNA

<213> ORGANISM: Homo sapiens

<400> SEQUENCE: 102
gacctgatgt tccacatgca g					21

<210> SEQ ID NO 103
<211> LENGTH: 21
<212> TYPE: DNA
<213> ORGANISM: Homo sapiens

<400> SEQUENCE: 103
gatgttccac atgcagaggc a					21

<210> SEQ ID NO 104
<211> LENGTH: 21
<212> TYPE: DNA
<213> ORGANISM: Homo sapiens

<400> SEQUENCE: 104
gactacggca tgtgcaagga a					21

<210> SEQ ID NO 105
<211> LENGTH: 21
<212> TYPE: DNA
<213> ORGANISM: Homo sapiens

<400> SEQUENCE: 105
gacatgaaca cagaggacta c					21

<210> SEQ ID NO 106
<211> LENGTH: 21
<212> TYPE: DNA
<213> ORGANISM: Homo sapiens

<400> SEQUENCE: 106
gacttgctgg agaagaagca g					21

<210> SEQ ID NO 107
<211> LENGTH: 21
<212> TYPE: DNA
<213> ORGANISM: Homo sapiens

<400> SEQUENCE: 107
gatcacagac gactacggtc t					21

<210> SEQ ID NO 108
<211> LENGTH: 21
<212> TYPE: DNA
<213> ORGANISM: Homo sapiens

<400> SEQUENCE: 108
gaggatcgac cagtcagagt t					21

<210> SEQ ID NO 109
<211> LENGTH: 21
<212> TYPE: DNA
<213> ORGANISM: Homo sapiens

<400> SEQUENCE: 109
gatcgaccag tcagagttcg a					21

<210> SEQ ID NO 110
<211> LENGTH: 21

<212> TYPE: RNA
<213> ORGANISM: Artificial
<220> FEATURE:
<223> OTHER INFORMATION: siRNA polynucleotide, synthesized

<400> SEQUENCE: 110
gcucugugag aagugagau u                                        21

<210> SEQ ID NO 111
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 111
ggaagugaga gacauguguu u                                       21

<210> SEQ ID NO 112
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 112
agugagagac augucguu u                                         21

<210> SEQ ID NO 113
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 113
gagacaugug ucgucugcau u                                       21

<210> SEQ ID NO 114
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 114
agauggagga agcuguaccu u                                       21

<210> SEQ ID NO 115
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 115
ccugcaggaa gcauauggau u                                       21

<210> SEQ ID NO 116
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 116

```
ggagacagau ggaauugcuu u                                              21

<210> SEQ ID NO 117
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 117
ggaccuuaag ccaguuaucu u                                              21

<210> SEQ ID NO 118
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 118
ugacgaggau auugacuggu u                                              21

<210> SEQ ID NO 119
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 119
uuacacuccu gcuuccagau u                                              21

<210> SEQ ID NO 120
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 120
cgacaagucg guuguuccuu u                                              21

<210> SEQ ID NO 121
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 121
caagucgguu guuccugguu u                                              21

<210> SEQ ID NO 122
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 122
ccugauguuc cacaugcagu u                                              21

<210> SEQ ID NO 123
<211> LENGTH: 21
<212> TYPE: RNA
<213> ORGANISM: Artificial
```

```
<220> FEATURE:
<223> OTHER INFORMATION: siRNA polynucleotide, synthesized

<400> SEQUENCE: 123
uguuccacau gcagaggcau u                                              21

<210> SEQ ID NO 124
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 124
cuacggcaug ugcaaggaau u                                              21

<210> SEQ ID NO 125
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 125
caugaacaca gaggacuacu u                                              21

<210> SEQ ID NO 126
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 126
cuugcuggag aagaagcagu u                                              21

<210> SEQ ID NO 127
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 127
ucacagacga cuacggucuu u                                              21

<210> SEQ ID NO 128
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 128
ggaucgacca gucagaguuu u                                              21

<210> SEQ ID NO 129
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 129
ucgaccaguc agaguucgau u                                              21
```

```
<210> SEQ ID NO 130
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 130
uucgagacac uccuucacuc u                                              21

<210> SEQ ID NO 131
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 131
uuccuucacu cucuguacac a                                              21

<210> SEQ ID NO 132
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 132
uuucacucuc uguacacagc a                                              21

<210> SEQ ID NO 133
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 133
uucucuguac acagcagacg u                                              21

<210> SEQ ID NO 134
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 134
uuucuaccuc cuucgacaug g                                              21

<210> SEQ ID NO 135
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 135
uuggacgucc uucguauacc u                                              21

<210> SEQ ID NO 136
<211> LENGTH: 21
<212> TYPE: RNA
<213> ORGANISM: Artificial
<220> FEATURE:
<223> OTHER INFORMATION: siRNA polynucleotide, synthesized
```

```
<400> SEQUENCE: 136
uuccucuguc uaccuuaacg a                                              21

<210> SEQ ID NO 137
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 137
uuccuggaau ucggucaaua g                                              21

<210> SEQ ID NO 138
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 138
uuacugcucc uauaacugac c                                              21

<210> SEQ ID NO 139
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 139
uuaaugugag gacgaagguc u                                              21

<210> SEQ ID NO 140
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 140
uugcuguuca gccaacaagg a                                              21

<210> SEQ ID NO 141
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 141
uuguucagcc aacaaggacc a                                              21

<210> SEQ ID NO 142
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 142
uuggacuaca agguguacgu c                                              21

<210> SEQ ID NO 143
```

```
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 143
uuacaaggug uacgucuccg u                                             21

<210> SEQ ID NO 144
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 144
uugaugccgu acacguuccu u                                             21

<210> SEQ ID NO 145
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 145
uuguacuugu gucuccugau g                                             21

<210> SEQ ID NO 146
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 146
uugaacgacc ucuucuucgu c                                             21

<210> SEQ ID NO 147
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 147
uuagugucug cugaugccag a                                             21

<210> SEQ ID NO 148
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 148
uuccuagcug gucagucuca a                                             21

<210> SEQ ID NO 149
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 149
```
uuagcuggtc agucucaagc u                          21

<210> SEQ ID NO 150
<211> LENGTH: 21
<212> TYPE: DNA
<213> ORGANISM: Homo sapiens

<400> SEQUENCE: 150
tagacgacaa gaacgaggac g                          21

<210> SEQ ID NO 151
<211> LENGTH: 21
<212> TYPE: DNA
<213> ORGANISM: Homo sapiens

<400> SEQUENCE: 151
tacagacaga gaagcacgtg t                          21

<210> SEQ ID NO 152
<211> LENGTH: 21
<212> TYPE: DNA
<213> ORGANISM: Homo sapiens

<400> SEQUENCE: 152
tacactcctg cttccagacg a                          21

<210> SEQ ID NO 153
<211> LENGTH: 21
<212> TYPE: DNA
<213> ORGANISM: Homo sapiens

<400> SEQUENCE: 153
tattgctgtc caccgaggag t                          21

<210> SEQ ID NO 154
<211> LENGTH: 21
<212> TYPE: DNA
<213> ORGANISM: Homo sapiens

<400> SEQUENCE: 154
taaccaccgc atatgcatgc c                          21

<210> SEQ ID NO 155
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 155
gacgacaaga acgaggacgu u                          21

<210> SEQ ID NO 156
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 156
cagacagaga agcacguguu u                          21

<210> SEQ ID NO 157

```
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 157
cacuccugcu uccagacgau u                                              21

<210> SEQ ID NO 158
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 158
uugcugucca ccgaggaguu u                                              21

<210> SEQ ID NO 159
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 159
accaccgcau augcaugccu u                                              21

<210> SEQ ID NO 160
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 160
uucugcuguu cuugcuccug c                                              21

<210> SEQ ID NO 161
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 161
uugucugucu cuucgugcac a                                              21

<210> SEQ ID NO 162
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 162
uugugaggac gaaggucugc u                                              21

<210> SEQ ID NO 163
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 163
```

-continued

```
uuaacgacag guggcuccuc a                                                21

<210> SEQ ID NO 164
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 164
uuugguggcg uauacguacg g                                                21
```

PROTEIN KINASE C ZETA AS A DRUG TARGET FOR ARTHRITIS AND OTHER INFLAMMATORY DISEASES

This application claims the benefit of U.S. Provisional Application Ser. No. 60/468,987, filed May 8, 2003, and U.S. Provisional Application Ser. No. 60/491,274, filed Jul. 31, 2003, both of which are incorporated herein by reference in their entireties.

BACKGROUND OF THE INVENTION

1. Field of the Invention

The present invention is directed to methods of diagnosing, prognosing, and monitoring the course of arthritis in a subject based on increased protein kinase C zeta (ζPKC) gene expression in arthritic tissue. The present invention further provides compounds that inhibit the expression of ζPKC for use as remedies in the treatment of arthritis.

2. Related Background Art

Protein kinase C zeta (ζPKC) is emerging as an important signal transduction component. There is growing literature suggesting that ζPKC is involved in the NF-κB and AP-1 pathways. For example, a ζPKC knockout mouse is fully viable but displays a phenotype reminiscent of the tumor necrosis factor (TNF) receptor and lymphotoxin receptor knockouts, with severe impairment of NF-κB-dependent transcriptional activity (Leitges et al. (2001) *Mol. Cell* 8:771-80). Other investigators (Lallena et al. (1999) *Mol. Cell. Biol.* 19:2180-88) have shown a role for ζPKC in activating IκB and, thereby, activating NF-κB.

NF-κB activation has been implicated in numerous inflammatory disorders, including asthma, inflammatory bowel disease, and arthritis (reviewed in Roshak et al. (2002) *Curr. Opin. Pharmacol.* 2:316-21). NF-κB has been shown to play an essential role in the secretion of various matrix metalloproteinases (MMPs) from various cell types (Bond et al. (1998) *FEBS Lett.* 435:29-34; Bond et al. (1999) *Biochem. Biophys. Res. Commun.* 264:561-67; Bond et al. (2001) *Cardiovasc. Res.* 50:556-65). In arthritis, cytokines such as TNF and interleukin-1 (IL-1) increase the production and synthesis of MMPs and other degradative enzymes above levels that can be naturally controlled, resulting in disease (reviewed in Smith (1999) *Front. Biosci.* 4:D704; Mort and Billington (2001) *Arthritis Res.* 3:337-41; Catterall and Cawston (2003) *Arthritis Res. Ther.* 5:12-24).

To date, there has been no direct evidence linking ζPKC to arthritis. If ζPKC were expressed in affected tissues, however, it would help to explain the degradative actions of TNF and IL-1 by transducing the extracellular receptor binding of these factors to the intracellular induction of synthesis of degradative enzymes by NF-κB. In this regard, inhibitors of ζPKC may block TNF and IL-1 action and serve as treatments for arthritis and other inflammatory diseases. Such ζPKC inhibitors should be more efficacious than traditional cytokine and MMP inhibitors because they should ultimately affect more than just one target (Roshak, supra; Smith, supra). Such ζPKC inhibitors should also be safer than NF-κB inhibitors because ζPKC is only one of many effectors in the NF-κB pathway.

SUMMARY OF THE INVENTION

The present invention is based on the discovery that ζPKC expression is increased in the tissues of arthritis patients as compared to normal individuals. The present invention provides compounds that inhibit the expression of ζPKC in arthritic tissue including, but not limited to, inhibitory polynucleotides and polypeptides, small molecules, and peptide inhibitors. The present invention further provides methods of diagnosing, prognosing, and monitoring the course of arthritis based on aberrant ζPKC gene expression in arthritic tissue, as well as therapies for use as remedies for such aberrant expression. In addition, the present invention provides pharmaceutical formulations and routes of administration for such remedies, as well as methods for assessing the efficacy of such remedies.

In one embodiment, the invention provides a method for use in the diagnosis of arthritis in a subject comprising the steps of detecting a test amount of a ζPKC gene product in a sample from the subject; and comparing the test amount with a normal amount of the ζPKC gene product in a control sample, whereby a finding that the test amount is greater than the normal amount provides a positive indication in the diagnosis of arthritis. In a preferred embodiment, the sample comprises chondrocytes. In some other preferred embodiments, the ζPKC gene product comprises RNA or cDNA, or is ζPKC polypeptide.

In another embodiment, the invention provides a method for use in the prognosis of arthritis in a subject comprising the steps of detecting a test amount of a ζPKC gene product in a sample from the subject; and comparing the test amount with prognostic amounts of the ζPKC gene product in control samples, whereby a comparison of the test amount with the prognostic amounts provides an indication of the prognosis of arthritis. In a preferred embodiment, the sample comprises chondrocytes. In some other preferred embodiments, the ζPKC gene product comprises RNA or cDNA, or is ζPKC polypeptide.

In another embodiment, the invention provides a method for use in monitoring the course of arthritis in a subject comprising the steps of detecting a first test amount of a ζPKC gene product in a sample from the subject at a first time; detecting a second test amount of the ζPKC gene product in a sample from the subject at a second, later time; and comparing the first test amount and the second test amount, whereby an increase in the amount of the ζPKC gene product in the second test amount as compared with the first test amount indicates progression of arthritis, and whereby a decrease in the amount of the ζPKC gene product in the second test amount as compared with the first test amount indicates remission of arthritis. In a preferred embodiment, the sample comprises chondrocytes. In some other preferred embodiments, the ζPKC gene product comprises RNA or cDNA, or is ζPKC polypeptide.

In another embodiment, the invention provides a method for assessing the efficacy of a treatment for arthritis in a subject comprising the steps of detecting a first test amount of a ζPKC gene product in a sample from the subject prior to treatment; detecting a second test amount of the ζPKC gene product in a sample from the subject after treatment; and comparing the first test amount and the second test amount, whereby a decrease in the amount of the ζPKC gene product in the second test amount as compared with the first test amount indicates that the treatment for arthritis is efficacious. In a preferred embodiment, the sample comprises chondrocytes. In some other preferred embodiments, the ζPKC gene product comprises RNA or cDNA, or is ζPKC polypeptide.

In another embodiment, the invention provides a method of screening for a compound capable of inhibiting arthritis in a subject comprising the steps of providing a first sample and a second sample containing equivalent amounts of ζPKC; contacting the first sample with the compound; and determining whether the activity of ζPKC in the first sample is decreased relative to the activity of ζPKC in the second sample not contacted with the compound, whereby a decrease in the activity of ζPKC in the first sample as compared with the second sample indicates that the compound inhibits arthritis in the subject. In a preferred embodiment, the compound inhibits the activity of ζPKC in chondrocytes. In another preferred embodiment, the compound is a small molecule. In other preferred embodiments, the activity of ζPKC is determined by use of an enzymatic protein kinase assay, a chondrocyte pellet assay, an assay measuring proteoglycan degradation, or an assay measuring NF-κB activity.

In another embodiment, the invention provides a method of screening for a compound capable of inhibiting arthritis in a subject comprising the steps of providing a first sample and a second sample containing equivalent amounts of cells that express ζPKC; contacting the first sample with the compound; and determining whether the expression of ζPKC gene product in the first sample is decreased relative to the expression of ζPKC gene product in the second sample not contacted with the compound, whereby a decrease in the expression of ζPKC gene product in the first sample as compared with the second sample indicates that the compound inhibits arthritis in the subject. In a preferred embodiment, the compound inhibits the expression of ζPKC gene product in chondrocytes. In another preferred embodiment, the compound is a small molecule. In other preferred embodiments, the expression of ζPKC gene product is determined by use of an enzymatic protein kinase assay, a chondrocyte pellet assay, an assay measuring proteoglycan degradation, or an assay measuring NF-κB activity.

In another embodiment, the invention provides a method for the treatment of arthritis in a subject comprising administering to the subject a compound that inhibits the activity of ζPKC in the subject. In a preferred embodiment, the compound inhibits the activity of ζPKC in chondrocytes. In another preferred embodiment, the compound is an antisense polynucleotide. In another preferred embodiment, the compound is a small molecule. In another preferred embodiment, the compound is a siRNA molecule. In a further preferred embodiment, the siRNA molecule is selected from the group consisting of siRNA molecules shown in FIG. 1.

In another embodiment, the invention provides a method for the treatment of arthritis in a subject comprising administering to the subject a compound that inhibits the expression of ζPKC in the subject. In a preferred embodiment, the compound inhibits the expression of ζPKC in chondrocytes. In another preferred embodiment, the compound is an antisense polynucleotide. In another preferred embodiment, the compound is a small molecule. In another preferred embodiment, the compound is a siRNA molecule. In a further preferred embodiment, the siRNA molecule is selected from the group consisting of siRNA molecules shown in FIG. 1.

In another embodiment, the invention provides a siRNA molecule that inhibits the expression or activity of ζPKC. In a preferred embodiment, the siRNA molecule is selected from the group consisting of siRNA molecules shown in FIG. 1.

BRIEF DESCRIPTION OF THE DRAWINGS

FIG. 1 shows preferred siRNA molecules targeted to human ζPKC mRNA for use in RNAi. Target segments [SEQ ID NOs:9-20; 45-59; 90-109; and 150-154] of the ζPKC transcripts are grouped according to their first two nucleotides (AA, CA, GA, or TA) and are shown in the 5'->3' orientation. "GC Ratio" refers to the percentage of total G+C nucleotides in each target segment; "Position" refers to the nucleotide position in the human ζPKC cDNA (SEQ ID NO:1) immediately preceding the beginning of each target segment. Prefeffed siRNA molecules (siRNA duplexes) are shown on the right side of the figure. Both the sense strand for each siRNA duplex [SEQ TD NOs:21-32; 60-74; 110-129; and 155-159] and the corresponding antisense strand [SEQ ID NOs:33-44; 75-89; 130-149; and 160-164] are shown in the 5'->3' orientation. For example, the siRNA molecule directed to the first target segment presented in the figure (i.e., SEQ ID NO:9) is the siRNA duplex of the sense and antisense strands identified (i.e., SEQ ID NO:21 and SEQ ID NO:33, respectively).

FIG. 5 shows that ζPKC is upregulated in human osteoarthritic articular cartilage. Panel A shows ζPKC mRNA levels using the HG-U95Av2 Affymetrix GeneChip® Array; panel B shows ζPKC mRNA levels using TaqMan PCR analysis.

FIG. 6 shows that adenoviral-mediated expression of ζPKC increases proteoglycan degradation. Panel A shows proteoglycan released into the media in the chondrocyte pellet assay in response to overexpression of ζPKC and GFP; panel B shows the effects of stimulation with suboptimal levels of the cytokine TNFα.

DETAILED DESCRIPTION OF THE INVENTION

Figure 2:
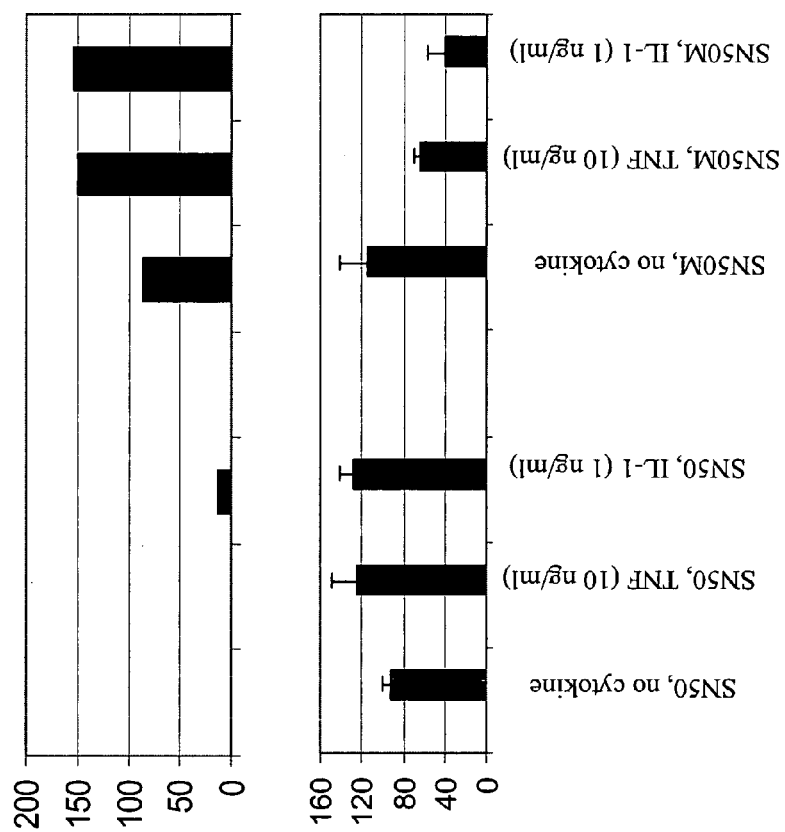
FIG. 2 is a graph depicting the effects of the NF-κB blocker SN50 (300 μg/ml), or its inactive analog SN50M (300 μg/ml), on TNF- or IL-1-mediated proteoglycan degradation in primary bovine chondrocytes in culture. The top panel shows proteoglycan content released in the media (μg/0.5 ml); the bottom panel shows proteoglycan content retained in the cell pellet (μg/ml).

We have discovered that ζPKC expression is upregulated in the tissues of arthritis patients as compared to normal individuals. The discovery that this enzyme is upregulated in arthritic tissue enables methods for diagnosing arthritis by detecting an increase in ζPKC expression and methods for treating arthritis by downregulating ζPKC expression. In addition, this discovery enables the identification of new ζPKC inhibitors useful in the treatment of arthritis.

Methods for Diagnosing, Prognosing, and Monitoring the Progress of Arthritis

Introduction

The present invention provides methods for diagnosing arthritis by detecting the upregulation of ζPKC. "Diagnostic" or "diagnosing" means identifying the presence or absence of a pathologic condition. Diagnostic methods involve detecting upregulation of ζPKC by determining a test amount of ζPKC gene product (e.g., mRNA, cDNA, or polypeptide, including fragments thereof) in a biological sample from a subject (human or nonhuman mammal), and comparing the test amount with a normal amount or range (i.e., an amount or range from an individual(s) known not to suffer from arthritis) for the ζPKC gene product. While a particular diagnostic method may not provide a definitive diagnosis of arthritis, it suffices if the method provides a positive indication that aids in diagnosis.

The present invention also provides methods for prognosing arthritis by detecting the upregulation of ζPKC. "Prognostic" or "prognosing" means predicting the probable development and/or severity of a pathologic condition. Prognostic methods involve determining the test amount of a ζPKC gene product in a biological sample from a subject, and comparing the test amount to a prognostic amount or range (i.e., an amount or range from individuals with varying severities of arthritis) for the ζPKC gene product. Various amounts of the ζPKC gene product in a test sample are consistent with certain prognoses for arthritis. The detection of an amount of ζPKC gene product at a particular prognostic level provides a prognosis for the subject.

The present invention also provides methods for monitoring the course of arthritis by detecting the upregulation of ζPKC. Monitoring methods involve determining the test amounts of a ζPKC gene product in biological samples taken from a subject at a first and second time, and comparing the amounts. A change in amount of ζPKC gene product between the first and second time indicates a change in the course of arthritis, with a decrease in amount indicating remission of arthritis, and an increase in amount indicating progression of arthritis. Such monitoring assays are also useful for evaluating the efficacy of a particular therapeutic intervention (e.g., disease attenuation vs. reversal) in patients being treated for arthritis.

Biological Sample Collection

Increased expression of ζPKC can be detected in a variety of biological samples, including cells (e.g., whole cells, cell fractions, and cell extracts) and tissues. Biological samples also include sections of tissue such as biopsies and frozen sections taken for histological purposes. Preferred biological samples include articular cartilage (i.e., chondrocytes), synovium, and synovial fluid.

Normal, Diagnostic, and Prognostic Values

In the diagnostic and prognostic assays of the present invention, the ζPKC gene product is detected and quantified to yield a test amount. The test amount is then compared to a normal amount or range. An amount above the normal amount or range (e.g., a 30% or greater increase (with $p<0.01$), or a 100% or greater increase (with $p<0.05$)) is a positive sign in the diagnosis of arthritis. Particular methods of detection and quantitation of ζPKC gene products are described below.

Normal amounts or baseline levels of ζPKC gene products can be determined for any particular sample type and population. Generally, baseline (normal) levels of ζPKC protein or mRNA are determined by measuring the amount of ζPKC protein or mRNA in a biological sample type from normal (i.e., healthy) subjects. Alternatively, normal values of ζPKC gene product can be determined by measuring the amount in healthy cells or tissues taken from the same subject from which the diseased (or possibly diseased) test cells or tissues were taken. The amount of ζPKC gene product (either the normal amount or the test amount) can be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values of ζPKC gene product because relative values are sufficient for many applications of these methods. It will also be appreciated that in addition to the quantity or abundance of ζPKC gene products, variant or abnormal ζPKC gene products or their expression patterns (e.g., mutated transcripts, truncated polypeptides) may be identified by comparison to normal gene products and expression patterns.

Assays for ζPKC Gene Products

The diagnostic, prognostic, and monitoring assays of the present invention involve detecting and quantifying ζPKC gene products in biological samples. ζPKC gene products include, for example, ζPKC mRNA and ζPKC polypeptide, and both can be measured using methods well known to those skilled in the art.

For example, ζPKC mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention are based on the nucleic acid sequence of ζPKC and are well known in the art.

Alternatively, ζPKC mRNA can be amplified before detection and quantitation. Such amplification-based assays are well known in the art and include polymerase chain reaction (PCR), reverse-transcription-PCR (RT-PCR), PCR-enzyme-linked immunosorbent assay (PCR-ELISA), and ligase chain reaction (LCR). Primers and probes for producing and detecting amplified ζPKC gene products (e.g., mRNA or cDNA) may be readily designed and produced without undue experimentation by those of skill in the art based on the nucleic acid sequence of ζPKC. Amplified ζPKC gene products may be directly analyzed, e.g., by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that whichever amplification method is used, a variety of quantitative methods known in the art (e.g., quantitative PCR) may be used if quantitation of ζPKC gene products is desired.

ζPKC polypeptide (or fragments thereof) can be detected and quantified using various well-known enzymatic and immunological assays. Enzymatic assays refer to assays that utilize ζPKC substrates to detect protein kinase activity. Various natural and artificial substrates useful for detecting and quantifying ζPKC activity are known, and include myristoyl alanine-rich C kinase substrate (MARCKS) peptide (Herget et al. (1995) *Eur. J. Biochem.* 233:448-57), p47phox (Dang et al. (2001) *J. Immunol.* 166:1206-13), myelin basic protein (Kim et al. (2002) *J. Biol. Chem.* 277:30375-81), protamine sulfate (McGlynn et al. (1992) *J. Cell. Biochem.* 49:239-50), nucleolin (Zhou et al. (1997) *J. Biol. Chem.* 272:31130-37); heterogeneous ribonucleoprotein AI (hnRNPA1) (Municio et al. (1995) *J. Biol. Chem.* 270:15884-91), ζPKC-derived peptide (Kochs et al. (1993) *Eur. J. Biochem.* 216:597-606), and ζPKC-derived peptide (Standaert et al. (1999) *J. Biol. Chem.* 274:14074-78). Numerous enzymatic assay protocols (radioactive and nonradioactive) suitable for detecting and quantifying ζPKC activity are described in the literature and/or are commercially available in kit form from, e.g., PanVera (Madison, Wis.), Promega (Madison, Wis.), Transbio (Baltimore, Md.), Upstate (Waltham, Mass.), and Research & Diagnostic Antibodies (Benicia, Calif.).

Immunological assays refer to assays that utilize an antibody (e.g., polyclonal, monoclonal, chimeric, humanized, scFv, and fragments thereof) that specifically binds to ζPKC polypeptide (or a fragment thereof). A number of well-established immunological assays suitable for the practice of the present invention are known, and include ELISA, radioimmunoassay (RIA), immunoprecipitation, immunofluorescence, and Western blotting.

The anti-ζPKC antibodies (preferably anti-mammalian ζPKC; more preferably anti-human ζPKC) to be used in the immunological assays of the present invention are commercially available from, e.g., Sigma-Aldrich (St. Louis, Mo.), Upstate (Waltham, Mass.), and Research Diagnostics (Flanders, N.J.). Alternatively, anti-ζPKC antibodies may be produced by methods well known to those skilled in the art. For example, monoclonal antibodies to ζPKC (preferably mammalian; more preferably human (e.g., GenBank Acc. No. Q05513; SEQ ID NO:2)) can be produced by generation of hybridomas in accordance with known methods. Hybridomas formed in this manner are then screened using standard methods, such as ELISA, to identify one or more hybridomas that produce an antibody that specifically binds to ζPKC. Full-length ζPKC may be used as the immunogen, or, alternatively, antigenic peptide fragments of ζPKC may be used.

As an alternative to preparing monoclonal antibody-secreting hybridomas, a monoclonal antibody to ζPKC may be identified and isolated by screening a recombinant combinatorial immunoglobulin library (e.g., an antibody phage display library) to thereby isolate immunoglobulin library members that bind to ζPKC. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with ζPKC (preferably mammalian; more preferably human) or an antigenic fragment thereof. The antibody titer in the immunized subject may be monitored over time by standard techniques, such as with ELISA, using immobilized marker protein. If desired, the antibody molecules directed against ζPKC may be isolated from the subject or culture media and further purified by well-known techniques, such as protein A chromatography, to obtain an IgG fraction.

Fragments of antibodies to ζPKC may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to ζPKC, comprising both human and nonhuman portions, may be produced using standard recombinant DNA techniques. Humanized antibodies to ζPKC may also be produced using transgenic mice that are incapable of expressing endogenous immunoglobulin heavy and light chain genes, but which can express human heavy and light chain genes.

In the immunological assays of the present invention, the ζPKC polypeptide is typically detected directly (i.e., the anti-ζPKC antibody is labeled) or indirectly (i.e., a secondary antibody that recognizes the anti-ζPKC antibody is labeled) using a detectable label. The particular label or detectable group used in the assay is usually not critical, as long as it does not significantly interfere with the specific binding of the antibodies used in the assay.

The immunological assays of the present invention may be competitive or noncompetitive. In competitive assays, the amount of ζPKC in a sample is measured indirectly by measuring the amount of added (exogenous) ζPKC displaced from a capture agent (i.e., an anti-ζPKC antibody) by the ζPKC in the sample. In noncompetitive assays, the amount of ζPKC in a sample is directly measured. In a preferred noncompetitive "sandwich" assay, the capture agent (e.g., a first anti-ζPKC antibody) is bound directly to a solid support (e.g., membrane, microtiter plate, test tube, dipstick, glass or plastic bead) where it is immobilized. The immobilized agent then captures any ζPKC polypeptide present in the sample. The immobilized ζPKC can then be detected using a second labeled anti-ζPKC antibody. Alternatively, the second anti-ζPKC antibody can be detected using a labeled secondary antibody that recognizes the second anti-ζPKC antibody.

Screening Methods for Identifying Compounds that Inhibit ζPKC Expression and/or Activity Introduction The present invention provides methods (also referred to herein as "screening assays") for identifying novel compounds (e.g., small molecules) that inhibit expression of PKC in arthritic tissue. In one embodiment, cells that express ζPKC (either naturally or recombinantly) are contacted with a test compound to determine whether the compound inhibits expression of a ζPKC gene product (e.g., mRNA or polypeptide), with a decrease in expression (as compared to an untreated sample of cells) indicating that the compound inhibits ζPKC in arthritic tissue. Changes in ζPKC gene expression can be determined by any method known in the art or described above. In a preferred embodiment, cells transfected with a reporter construct comprising a marker gene (e.g., luciferase or green fluorescent protein (GFP)) downstream of a NF-κB binding site are contacted with a test compound to determine whether the compound can inhibit expression of the marker protein when the cells are treated with cytokines. Compounds identified that inhibit ζPKC or marker protein expression are candidates as drugs for the prophylactic and therapeutic treatment of arthritis.

Alternatively, compounds can be identified that inhibit the kinase activity of ζPKC in vitro using assays described previously. Purified (or partially purified) ζPKC is contacted with a test compound to determine whether the compound inhibits the kinase activity of ζPKC (as compared to an untreated sample of enzyme). Compounds identified that inhibit ζPKC activity could then be tested in in vitro and in vivo models of arthritis. Several in vitro models are described in the Examples below. In vivo models of arthritis include, but are not limited to, the anterior cruciate ligament resection models in the dog and rabbit, and the partial meniscectomy models in the rabbit and mouse. Exemplary methods and assays for directly and indirectly measuring the activity of ζPKC and/or for determining inhibition of the activity of ζPKC include, but are not limited to, enzymatic protein kinase activity assays (as detailed above), chondrocyte pellet assays, assays measuring proteoglycan degradation, and assays measuring NF-κB activity.

Sources of ζPKC

The ζPKC (preferably mammalian; more preferably human (e.g., GenBank Acc. No. Q05513; SEQ ID NO:2)) to be used in the screening assays of the current invention are commercially available from, e.g., Sigma-Aldrich, (St. Louis, Mo.), Research Diagnostics (Flanders, N.J.), ProQinase (Freiburg, Germany), and PanVera (Madison, Wis.). Alternatively, ζPKC can be purified or partially purified from various tissues (preferably mammalian; more preferably human), including brain, placenta, testes and lung, using known purification processes such as gel filtration and ion exchange chromatography. Purification may also include affinity chromatography with agents known to bind ζPKC (e.g., anti-ζPKC antibodies). These purification processes may also be used to purify ζPKC from recombinant sources.

Polynucleotides encoding ζPKC (or enzymatic portions thereof) may be operably linked to an appropriate expression control sequence for recombinant production of ζPKC. The ζPKC polynucleotides are preferably of mammalian origin (e.g., mouse ζPKC cDNA (GenBank Acc. No. M94632); rat ζPKC cDNA (GenBank Acc. No. J04532); rabbit ζPKC cDNA (GenBank Acc. No. U78768)), and more preferably of human origin (e.g., human ζPKC cDNA (GenBank Acc. No. NM_002744; SEQ ID NO:1)). General methods for expressing these recombinant ζPKC polynucleotides are well known in the art.

A number of cell lines may act as suitable host cells for recombinant expression of ζPKC. Mammalian host cell lines include, for example, COS cells, CHO cells, 293 cells, A431 cells, 3T3 cells, CV-1 cells, HeLa cells, L cells, BHK21 cells, HL-60 cells, U937 cells, HaK cells, and Jurkat cells, as well as normal diploid cells, cell strains derived from in vitro culture of primary tissue, and primary explants.

Alternatively, ζPKC (or enzymatic portions thereof) may be recombinantly produced in lower eukaryotes such as yeast or in prokaryotes. Potentially suitable yeast strains include *Saccharomyces cerevisiae, Schizosaccharomyces pombe, Kluyveromyces* strains, and *Candida* strains. Potentially suitable bacterial strains include *Escherichia coli, Bacillus subtilis*, and *Salmonella typhimurium*. If the polypeptides of the present invention are made in yeast or bacteria, it may be necessary to modify them by, for example, phosphorylation or glycosylation of appropriate sites, in order to obtain functionality. Such covalent attachments may be accomplished using well-known chemical or enzymatic methods.

ζPKC (or enzymatic portions thereof) may also be recombinantly produced using insect expression vectors, such as baculovirus vectors, and employing an insect cell expression system. Materials and methods for baculovirus/Sf9 expression systems are commercially available in kit form (e.g., the MaxBac® kit, Invitrogen, Carlsbad, Calif.).

In order to facilitate purification, ζPKC (or enzymatic portions thereof) may be recombinantly expressed as fusions with proteins such as maltose-binding protein (MBP), glutathione-S-transferase (GST), or thioredoxin (TRX). Kits for expression and purification of such fusion proteins are commercially available from New England BioLabs (Beverly, Mass.), Pharmacia (Piscataway, N.J.), and Invitrogen (Carlsbad, Calif.), respectively. ζPKC can also be tagged with a small epitope and subsequently identified or purified using a specific antibody to the epitope. One such epitope is the FLAG epitope, which is commercially available from Eastman Kodak (New Haven, Conn.).

ζPKC (or enzymatic portions thereof) may also be produced by known conventional chemical synthesis. Methods for chemically synthesizing polypeptides are well known to those skilled in the art. Such chemically synthetic ζPKC should possess biological properties in common with the naturally produced form, and thus can be employed as a biologically active or immunological substitute for natural ζPKC.

Sources and Screening of Test Compounds

The test compounds of the present invention may be obtained from a number of sources. For example, combinatorial libraries of molecules are available for screening. Using such libraries, thousands of molecules can be screened for inhibitory activity. Preparation and screening of compounds can be screened as described above or by other methods well known to those of skill in the art. The compounds thus identified can serve as conventional "lead compounds" or can be used as the actual therapeutics.

Methods of Treatment

Introduction

The present invention provides both prophylactic and therapeutic methods for the treatment of arthritis by inhibiting expression and/or activity of ζPKC. The methods involve contacting cells (either in vitro, in vivo, or ex vivo) with an agent in an amount effective to inhibit expression and/or activity of ζPKC. The agent can be any molecule that inhibits expression and/or activity of ζPKC, including, but not limited to, inhibitory polynucleotides, small molecules, inhibitory protein biologics, and peptide inhibitors.

Inhibitory Polynucleotides

Decreased expression of ζPKC in an organism afflicted with (or at risk for) arthritis, or in an involved cell from such an organism, may be achieved through the use of various inhibitory polynucleotides, such as antisense polynucleotides and ribozymes, that bind and/or cleave the mRNA transcribed from the ζPKC gene (e.g., Galderisi et al. (1999) *J. Cell Physiol.* 181:251-57; Sioud (2001) *Curr. Mol. Med.* 1:575-88).

The antisense polynucleotides or ribozymes of the invention can be complementary to an entire coding strand of ζPKC, or to a portion thereof. Alternatively, antisense polynucleotides or ribozymes can be complementary to a noncoding region of the coding strand of ζPKC. The antisense polynucleotides or ribozymes can be constructed using chemical synthesis and enzymatic ligation reactions using procedures well known in the art. The nucleoside linkages of chemically synthesized polynucleotides can be modified to enhance their ability to resist nuclease-mediated degradation, as well as to increase their sequence specificity. Such linkage modifications include, but are not limited to, phosphorothioate, methylphosphonate, phosphoroamidate, boranophosphate, morpholino, and peptide nucleic acid (PNA) linkages (Galderisi et al., supra; Heasman (2002) *Dev. Biol.* 243:209-14; Micklefield (2001) *Curr. Med. Chem.* 8:1157-79). Alternatively, these molecules can be produced biologically using an expression vector into which a polynucleotide of the present invention has been subcloned in an antisense (i.e., reverse) orientation.

The inhibitory polynucleotides of the present invention also include triplex-forming oligonucleotides (TFOs) which bind in the major groove of duplex DNA with high specificity and affinity (Knauert and Glazer (2001) *Hum. Mol. Genet.* 10:2243-51). Expression of ζPKC can be inhibited by targeting TFOs complementary to the regulatory regions of the ζPKC gene (i.e., the promoter and/or enhancer sequences) to form triple helical structures that prevent transcription of the ζPKC gene.

In a preferred embodiment, the inhibitory polynucleotides of the present invention are short interfering RNA (siRNA) molecules. siRNA molecules are short (preferably 19-25 nucleotides; most preferably 19 or 21 nucleotides), double-stranded RNA molecules that cause sequence-specific degradation of target mRNA. This degradation is known as RNA interference (RNAi) (e.g., Bass (2001) *Nature* 411:428-29). Originally identified in lower organisms, RNAi has been effectively applied to mammalian cells and has recently been shown to prevent fulminant hepatitis in mice treated with siRNAs targeted to Fas mRNA (Song et al. (2003) *Nature Med.* 9:347-51). In addition, intrathecally delivered siRNA has recently been reported to block pain responses in two models (agonist-induced pain model and neuropathic pain model) in the rat (Dorn et al. (2004) *Nucleic Acids Res.* 32(5):e49).

The siRNA molecules of the present invention can be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) *Proc. Natl. Acad. Sci. USA* 99:6047-52). The siRNA molecules can be chemically synthesized (Elbashir et al. (2001) *Nature* 411:494-98) or produced by in vitro transcription using single-stranded DNA templates (Yu et al., supra). Alternatively, the siRNA molecules can be produced biologically, either transiently (Yu et al., supra; Sui et al. (2002) *Proc. Natl. Acad. Sci. USA* 99:5515-20) or stably (Paddison et al. (2002) *Proc. Natl. Acad. Sci. USA* 99:1443-48), using an expression vector(s) containing the sense and antisense siRNA sequences. Recently, reduction of levels of target mRNA in primary human cells, in an efficient and sequence-specific manner, was demonstrated using adenoviral vectors that express hairpin RNAs, which are further processed into siRNAs (Arts et al. (2003) *Genome Res.* 13:2325-32).

The siRNA molecules targeted to the polynucleotides of the present invention can be designed based on criteria well known in the art (e.g., Elbashir et al. (2001) *EMBO J.* 20:6877-88). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; and the target segment preferably should be in the ORF region of the target mRNA and preferably should be at least 75 bp after the initiation ATG and at least 75 bp before the stop codon. Based on these criteria, preferred siRNA molecules of the present invention, targeted to human ζPKC mRNA, have been designed and are shown in FIG. 1. Other siRNA molecules targeted to ζPKC mRNAs can be designed by one of ordinary skill in the art using the aforementioned criteria or other known criteria (e.g., Reynolds et al. (2004) *Nature Biotechnol.* 22:326-30).

Small Molecules

Decreased expression of ζPKC in an organism afflicted with (or at risk for) arthritis, or in an involved cell from such an organism, may also be achieved through the use of small molecules (usually organic small molecules) that bind to and inhibit the activity of ζPKC. Small molecules known to inhibit the activity of PKC (preferably isoform specific) can be used in the treatment methods of the present invention. Numerous small molecules that inhibit PKC are known in the art (including ones approved for treatment of disease, as well as others in clinical trials), and include both natural (e.g., staurosporine) and artificial (e.g., LY333531) compounds (reviewed in Goekjian and Jirousek (2001) *Expert. Opin. Investing. Drugs* 10:2117-40; Way et al. (2000) *Trends Pharmacol. Sci.* 21:181-87, both of which are incorporated by reference herein). These molecules can be used directly or can serve as starting compounds for the development of improved PKC inhibitors (preferably isoform specific). Alternatively, novel small molecules (preferably isoform specific) identified by the screening methods described above may be used.

Inhibitory Protein Biologics

Decreased activity of ζPKC in an organism afflicted with (or at risk for) arthritis, or in an involved cell from such an organism, may also be achieved using protein biologics. Inhibitory protein biologics refer to protein molecules having inhibitory biological activity in a cell or organism. Preferred inhibitory protein biologics for use in the treatment methods of the present invention include Par4 and kinase-defective dominant-negative (DN) mutant forms of ζPKC. Par4 is a naturally occurring protein that binds to ζPKC, which serves to inhibit its enzymatic function (Diaz-Meco et al. (1996) *Cell* 86:777-86). DN mutant forms of ζPKC, such as rat ζPKC with a lysine 281 to tryptophan point mutation (Bandyopadhyay et al. (1997) *J. Biol. Chem.* 272:2551-58), reduce the activity of endogenous ζPKC by competing for substrate and can be made using well-known site-directed mutagenesis techniques. Any variant of ζPKC that lacks kinase activity but still inhibits ζPKC-mediated signal transduction may be used as a DN mutant. These inhibitory protein biologics may be generated in cells (preferably chondrocytes) in situ using the above-described expression techniques.

Peptide Inhibitors

Decreased activity of ζPKC in an organism afflicted with (or at risk for) arthritis, or in an involved cell from such an organism, may also be achieved using peptide inhibitors that bind to and inhibit the activity of ζPKC. Peptide inhibitors include peptide pseudosubstrates that prevent ζPKC from interacting with its substrates, as well as peptides that bind to either ζPKC or its substrates and block ζPKC-mediated phosphorylation. Peptide inhibitors that inhibit ζPKC are known in the literature and include SIYRRGARRWRKL (SEQ ID NO:3), SIYRRGARRWRKLYRAN (SEQ ID NO:4), and RRGARRWRK (SEQ ID NO:5) (e.g., Dang et al., supra; Zhou et al., supra). Preferably these peptide inhibitors are myristoylated (SEQ ID NOs:6, 7, and 8, respectively) to improve cell permeability (e.g., Standaert et al., supra; for SEQ ID NO:6). Myristoylated and nonmyristoylated ζPKC peptide inhibitors can be chemically synthesized and are commercially available from, e.g., Quality Controlled Biochemical (Hopkinton, Mass.) and BioSource International, Inc., USA (Camarillo, Calif.). One can provide a cell (preferably a chondrocyte) with a peptide inhibitor in vitro, in vivo, or ex vivo using the techniques described above.

Administration

Any of the compounds described herein (preferably a small molecule) can be administered in vivo in the form of a pharmaceutical composition for the treatment of arthritis. The pharmaceutical compositions may be administered by any number of routes, including, but not limited to, oral, nasal, rectal, topical, sublingual, intravenous, intramuscular, intraarterial, intramedullary, intrathecal, intraventricular, intraperitoneal, intraarticular, or transdermal routes. In addition to the active ingredients, the pharmaceutical compositions may contain pharmaceutically acceptable carriers comprising excipients, coatings, and auxiliaries known in the art.

For any compound, the therapeutically effective dose can be estimated initially either in cell culture or in animal models. The therapeutically effective dose refers to the amount of active ingredient that ameliorates the condition or its symptoms. Therapeutic efficacy and toxicity in cell cultures or animal models may be determined by standard pharmaceutical procedures (e.g., ED50: the dose therapeutically effective in 50% of the population; LD50: the dose lethal to 50% of the population). The dose ratio between therapeutic and toxic effects is the therapeutic index, and can be expressed as the ratio ED50/LD50. Pharmaceutical compositions that exhibit large therapeutic indexes are preferred.

The data obtained from cell culture and animal models can then be used to formulate a range of dosage for the compound for use in mammals, preferably humans. The dosage of such a compound preferably lies within a range of concentrations that include the ED50 with little to no toxicity. The dosage may vary within this range depending upon the composition form employed and the administration route utilized.

EXAMPLES

The Examples which follow are set forth to aid in the understanding of the invention but are not intended to, and should not be construed to, limit its scope in any way. The Examples do not include detailed descriptions of conventional methods, such as those employed in the construction of vectors and plasmids, the insertion of genes encoding polypeptides into such vectors and plasmids, the introduction of such vectors and plasmids into host cells, or the expression of polypeptides from such vectors and plasmids in host cells. Such methods, and other conventional methods, are well known to those of ordinary skill in the art.

Example 1

ζPKC Expression is Upregulated in Arthritis

Example 1.1

Experimental Design

To identify transcripts differentially expressed between arthritic and normal articular cartilage, tissue samples were obtained from arthritis patients with end-stage knee replacement and nonarthritic amputee individuals. The presence or absence of arthritis was confirmed by histology.

Example 1.2

Oligonucleotide Array Hybridization

The Human Genome U95Av2 (HG-U95Av2) GeneChip® Array (Affymetrix, Santa Clara, Calif.) was used for expression profiling. The HG-U95Av2 chip contains 25-mer oligo-nucleotide probes representing ~12,000 primarily full-length sequences (~16 probe pairs/sequence) derived from the human genome. For each probe designed to be perfectly complimentary to a target sequence, a partner probe is generated that is identical except for a single base mismatch in its center. These probe pairs allow for signal quantitation and subtraction of nonspecific noise.

RNA was extracted from individual articular cartilage tissue, converted to biotinylated cRNA, and fragmented according to the Affymetrix protocol. The fragmented cRNAs were diluted in 1×MES buffer containing 100 μg/ml herring sperm DNA and 500 μg/ml acetylated BSA and denatured for 5 min at 99° C. followed immediately by 5 min at 45° C. Insoluble material was removed from the hybridization mixtures by a brief centrifugation, and the hybridization mix was added to each array and incubated at 45° C. for 16 hr with continuous rotation at 60 rpm. After incubation, the hybridization mix was removed and the chips were extensively washed with 6×SSPET and stained with SAPE solution as described in the Affymetrix protocol.

Example 1.3

Oligonucleotide Array Data Analysis

The raw florescent intensity value of each transcript was measured at a resolution of 6 mm with a Hewlett-Packard Gene Array Scanner. GeneChip® software 3.2 (Affymetrix), which uses an algorithm to determine whether a gene is "present" or "absent," as well as the specific hybridization intensity values or "average differences" of each gene on the array, was used to evaluate the fluorescent data. The average difference for each gene was normalized to frequency values by referral to the average differences of 11 control transcripts of known abundance that were spiked into each hybridization mix according to the procedure of Hill et al. ((2000) *Science* 290:809-12). The frequency of each gene was calculated and represents a value equal to the total number of individual gene transcripts per $10^6$ total transcripts.

The frequency of each transcript was evaluated, and the transcript was included in the study if it met the following three criteria. First, transcripts which were called "present" by the GeneChip®(8 software in at least one of the arrays for both arthritis and normal cartilage were included in the analysis. Second, for comparison between arthritis and normal cartilage, a t-test was applied to identify the subset of transcripts that had a significant ($p<0.05$) increase or decrease in frequency values. Third, average-fold changes in frequency values across the statistically significant subset of transcripts were required to be 2.4-fold or greater. These criteria were established based upon replicate experiments that estimated the intraarray reproducibility.

Based on these criteria, 602 transcripts were identified that were differentially expressed in arthritic and normal articular cartilage. One such transcript identified was ζPKC.

Example 2

Inhibition of ζPKC Activity Inhibits Extracellular Matrix (ECM) Degradation

Example 2.1

Primary Bovine Chondrocyte Isolation and Culture

Full-thickness bovine articular cartilage slices were dissected under aseptic conditions, rinsed four times in PBS, and subjected to pronase and collagenase digestion (1 mg/ml pronase (Calbiochem, San Diego, Calif.) for 30 minutes and 1 mg/ml Collagenase P (Roche Diagnostics Corporation, Indianapolis, Ind.) overnight at 37° C. in DME without serum) to isolate chondrocytes embedded in the cartilage extracellular matrix. The digest was filtered through a 70 micron Falcon™ cell strainer (BD Biosciences, San Jose, Calif.) and washed twice in DME containing 10% FBS. Typically 2-4×10$^8$ cells were obtained from a calf metacarpophalangeal joint surface. Cells were plated in monolayer in six-well plates at density of 2×10$^6$ cells/well. For pellet culture, cells were resuspended in growth media [HL-1 media (Cambrex Corporation, East Rutherford, N.J.), penicillin+streptomycin, glutamine, 50 µg/ml ascorbate, and 10% FBS] at 1×10$^6$ cells/ml, and 1 ml aliquots of cells were transferred to 15 ml sterile Falcon centrifuge tubes. The cells were centrifuged at 200×g for 5 min at 4° C. and the resulting cell pellets were cultured as described previously (Xu et al. (1996) *Endocrinology* 137:3557-65). Cell media were collected and stored for collagen and proteoglycan assays, and cells were refed with fresh media (3 ml/well, 1 ml/tube) every 3-4 days. Pellet cultures were maintained for 3 weeks, at which time the pellets were harvested and either digested with 0.5 ml of 300 µg/ml papain at 65° C. for 3-6 hrs for dimethylmethylene blue (DMMB) dye assays or prepared for histology.

Example 2.2

Peptide Blocker of NF-κB Can Inhibit TNF- or IL-1-Mediated Proteoglycan Degradation To demonstrate that blocking NF-κB activity can inhibit proteoglycan degradation in our culture system, primary bovine chondrocytes were cultured with the NF-κB blocker SN50 for 4 days at a concentration of 300 µg/ml in the presence or absence of 10 ng/ml TNF or 1 ng/ml IL-1. Cells were incubated with the inhibitor for 3 hrs prior to the addition of either TNF or IL-1. SN50 is a peptide that contains the nuclear localization signal of NF-κB coupled to a stretch of hydrophobic amino acids to facilitate transport across lipid bilayers, and has been shown to block NF-κB-mediated transcription (e.g., Lin et al. (1995) *J. Biol. Chem.* 270:14255-58). SN50M, which served as a negative control, is the same peptide with amino acid changes to abolish NF-κB-blocking activity. SN50 and SN50M are available from, e.g., Biomol Research Laboratories, Inc. (Plymouth Meeting, Pa.).

As shown in FIG. 2, SN50M was ineffective at preventing TNF- and IL-1-mediated proteoglycan degradation in bovine chondrocytes, as measured by proteoglycan release into the media and decreased recovery in the cell pellet. In contrast, SN50 completely inhibited the cytokine-mediated degradation of proteoglycan. In addition, SN50 even prevented proteoglycan degradation in the absence of cytokine treatment, as compared to SN50M. These results demonstrate that blocking NF-κB, which controls the cytokine-mediated synthesis of collagenases and aggrecanases, inhibits proteoglycan degradation in primary bovine chondrocytes.

Example 2.3

ζPKC Inhibitors Block TNF-Mediated Proteoglycan Degradation

To determine whether ζPKC inhibitors can inhibit TNF-mediated proteoglycan degradation, primary bovine chondrocytes were cultured with various concentrations of TNF for 5 days with or without (1) the myristoylated ζPKC peptide pseudosubstrate [herein termed "2089"; synthesized in-house; equivalent to SEQ ID NO:6; available from, e.g., BioSource International, Inc., USA (Camarillo, Calif.)], or (2) the small molecule inhibitor Ro-31-8220 (Sigma-RBI, Natick, Mass.). The inhibitors were added 3 hrs prior to addition of TNF.

Figure 3:
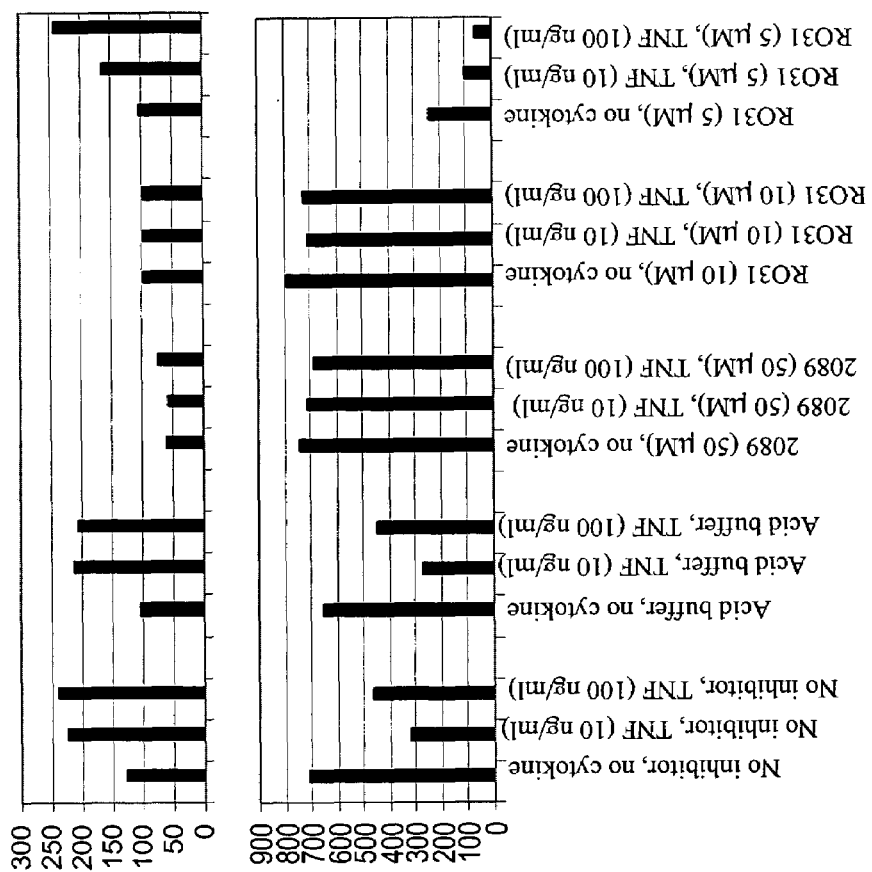
FIG. 3 is a graph depicting the effects of a myristoylated ζPKC pseudosubstrate peptide (2089) or PKC small molecule inhibitor Ro-31-8220 (RO31) on TNF-mediated proteoglycan degradation in primary bovine chondrocytes in culture. The top panel shows proteoglycan content released in the media (μg/0.5 ml); the bottom panel shows proteoglycan content retained in the cell pellet (μg/ml).

As shown in FIG. 3, TNF at 10 and 100 ng/ml caused significant proteoglycan degradation, as measured by proteoglycan release into the media and decreased recovery in the cell pellet. This proteoglycan degradation was significantly inhibited by both 50 µM 2089 and 10 µM Ro-31-8220 (RO31). In addition, these compounds inhibited proteoglycan degradation even in the absence of TNF, suggesting a blockade of constitutive levels of proteases. Ro-31-8220 at a concentration of 5 µM was relatively ineffective at preventing proteoglycan degradation. These results demonstrate that both 2089 and Ro-31-8220 penetrate the cell membrane of primary chondrocytes and effectively block TNF-mediated proteoglycan degradation. Trypan blue staining of the chondrocytes and lactate assays on the culture media were performed to rule out cytotoxicity as a possible explanation for the results. These experiments confirmed that the compounds do not cause appreciable cytotoxicity at the doses used in these experiments. In addition, control peptides were synthesized and tested in the same assay system to address the possibility that nonspecific effects may be causing the observed results. A nonmyristoylated version of the pseudosubstrate peptide, as well as a "scrambled control" peptide containing the same amino acid content as the pseudosubstrate peptide, but with a scrambled sequence, were tested, and both were found to be ineffective at blocking proteoglycan degradation.

Example 2.4

Myristoylated ζPKC Peptide Pseudosubstrate 2089 Blocks Both TNF- and IL-1-Mediated Proteoglycan Degradation in a Dose-Dependent Manner To determine whether myristoylated ζPKC peptide pseudosubstrate 2089 can inhibit cytokine-mediated proteoglycan degradation in a dose-dependent manner, primary bovine chondrocytes were cultured with either 10 ng/ml TNF or 1 ng/ml IL-1 for 4 days after addition of various concentrations of 2089.

Figure 4:
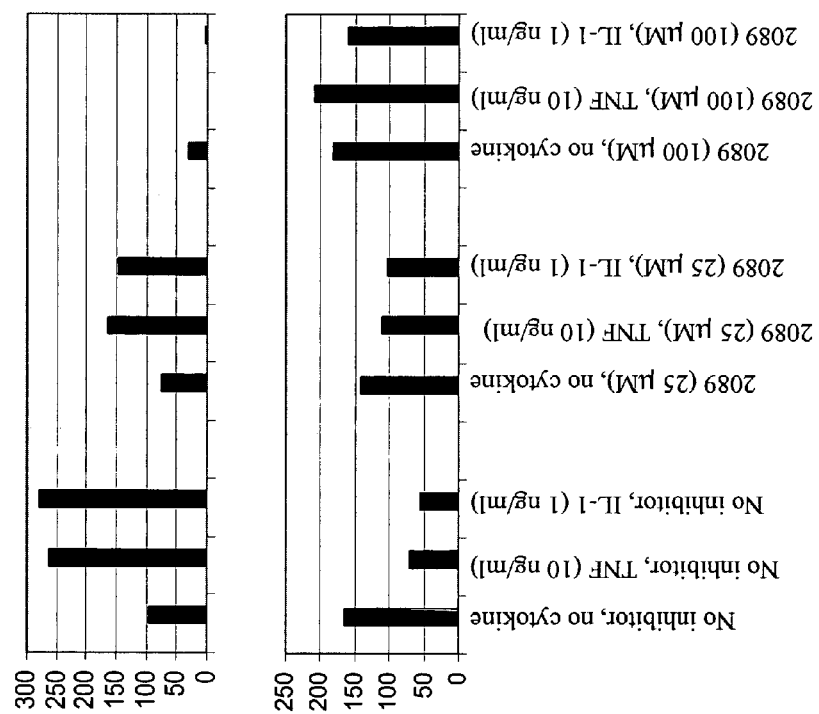
FIG. 4 is a graph depicting the dose-dependent effects of a myristoylated ζPKC pseudosubstrate peptide (2089) on TNF- or IL-1-mediated proteoglycan degradation in primary bovine chondrocytes in culture. The top panel shows proteoglycan content released in the media (μm/0.5 ml); the bottom panel shows proteoglycan content retained in the cell pellet (μg/ml).

As shown in FIG. 4, 2089 inhibited both TNF- and IL-1-mediated proteoglycan degradation in a dose-dependent manner, with the highest dose (100 µM) completely inhibiting proteoglycan release into the media. Again, increased cell pellet retention of proteoglycan and decreased release of proteoglycan into the media was achieved with 2089 even in the absence of cytokine. Cumulatively, these results indicate that inhibition of ζPKC in chondrocytes inhibits cytokine-mediated proteolytic degradation of proteoglycan. This, along with the fact that the ζPKC knockout mouse has a very benign phenotype (Leitges et al., supra), indicates that inhibition of ζPKC may be a safe, effective treatment for arthritis, as well as other inflammatory diseases.

Example 3

ζPKC mRNA is Upregulated in Human Osteoarthritic (OA) Cartilage

Transcriptional profiling data on human articular cartilage from osteoarthritic (OA) patients showed a statistically significant increase in ζPKC mRNA as compared with human non-OA cartilage. In panel A of FIG. 5, RNA was extracted from frozen pulverized articular cartilage tissue from clinical samples, and subjected to expression profiling analysis using the HG-U95Av2 chip. Three groups were analyzed: normal (non-OA) cartilage [13 samples]; severe OA cartilage (non-lesional areas) [29 samples]; and severe OA cartilage (lesional areas) [26 samples]. Levels of ζPKC mRNA were elevated in severe OA samples as compared with normal samples. In panel B of FIG. 5, TaqMan® Q-PCR (Applied Biosystems, Foster City, Calif.) analysis of the same set of samples showed significantly higher levels of ζPKC mRNA in severe OA samples as compared with normal samples; TaqMan® Q-PCR protocols were conducted according to the manufacturer's instructions.

Example 4

ζPKC Protein is Expressed in Chondrocytes

An anti-ζPKC antibody (nPKCζ(C-20); Santa Cruz Biotechnology, Inc., Santa Cruz, Calif.) was used to compare production of ζPKC protein in chondrocytes and Jurkat cells. The lysates of bovine chondrocytes and Jurkat cells (human cell line) were prepared by similar methods: cells were washed with cold phosphate-buffered saline and immediately placed in cell lysis buffer (Cell Signaling Technology, Inc., Beverly, Mass.) containing phosphatase inhibitors. Cells were incubated for 5 min on ice, and then centrifuged at 12,000 rpm for 10 min at 4° C. Samples were resolved by 12% SDS-polyacrylamide gel electrophoresis under reducing conditions. A Western blot showed that chondrocytes expressed a substantial amount of ζPKC protein; the same blot did not show appreciable expression of ζPKC protein in Jurkat cells.

Example 5

Adenoviral-Mediated Expression of ζPKC Increases Proteoglycan Degradation

Primary bovine chondrocytes were isolated and cultured as described above (in pellet format) in Example 2.1. Cells were cultured in 0.5 ml growth media (HL-1) containing 2% FBS prior to the addition of adenovirus (in 15 ml Falcon tubes). Adenovirus vectors containing ζPKC or GFP (green fluorescent protein) were prepared (Alden et al. (1999) *Hum. Gene Ther.* 10:2245-53), and cultures of chondrocytes were infected immediately following isolation and prior to pelleting. The adenovirus expressing GFP or ζPKC was added directly into the culture at a multiplicity of infection (MOI) of 5000. As seen in panel A of FIG. 6, overexpression of full-length ζPKC in primary bovine chondrocytes in culture (without addition of cytokines) resulted in a modest but statistically significant increase in proteoglycan degradation (as measured by proteoglycan released into the media in the chondrocyte pellet assay) as compared with overexpression of GFP. Medium containing 10% FBS was added to the culture after a 2-hour incubation at 37° C. (in a humidified atmosphere of 5% $CO_2$). The serum composition was gradually decreased every 3 days (sequentially to 5%, 2.5% and finally to 0% (serum-free) with every feeding of the chondrocyte pellets) to wean the cells from serum. Proteoglycan released into the media represents total proteoglycan released over 25 days.

In panel B of FIG. 6, proteoglycan was measured in the media over 4 days, with or without addition of cytokines, after cells had been weaned from serum. Addition of suboptimal levels of TNFα significantly enhanced the amount of proteoglycan released into the media in response to overexpression of ζPKC, as compared with overexpression of GFP or absence of adenovirus infection (FIG. 6, panel B).

Example 6

ζPKC is Responsible for TNFα-Mediated Proteoglycan Release in Chondrocytes

Figure 7:
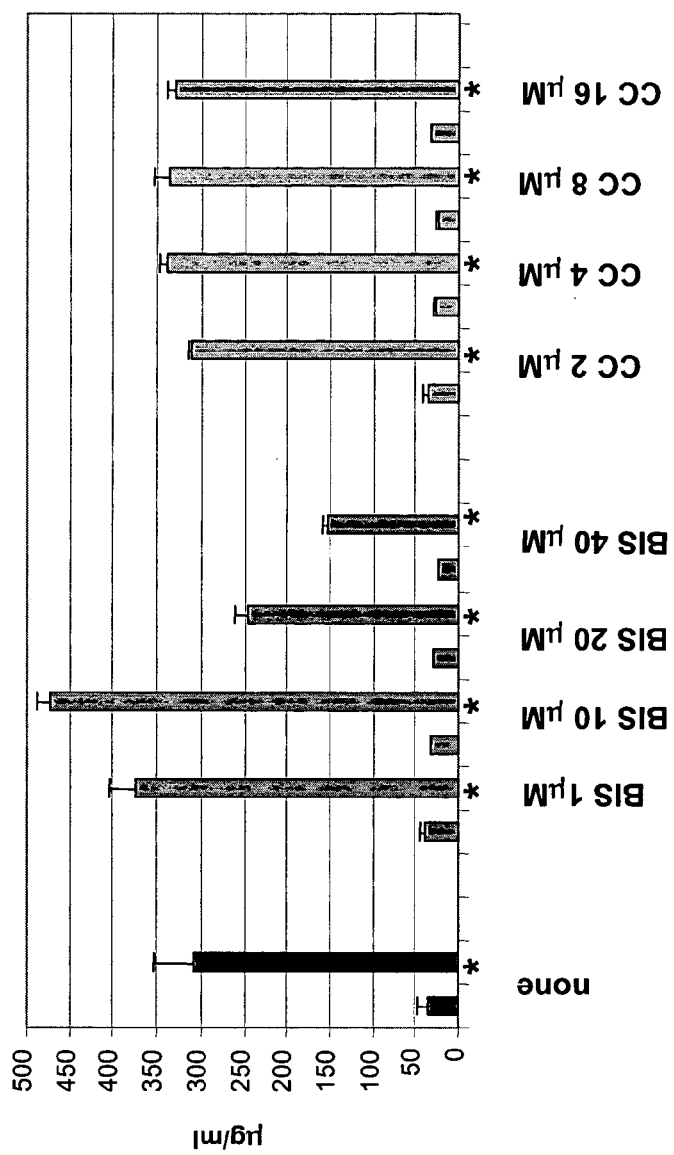
FIG. 7 demonstrates that ζPKC is responsible for TNFα-mediated proteoglycan release in articular chondrocytes. TNFα was added (100 ng/ml; denoted by *) to some cultures in the chondrocyte pellet assay. Two inhibitors were added at various doses: bisindolylmaleimide (BIS), a pan-PKC inhibitor; and chelerythrine chloride (CC), a competitive inhibitor of the phorbol ester-binding site that does not inhibit ζPKC. Proteoglycan release into the media is shown on the y-axis as μg/ml.

Articular bovine chondrocytes were prepared as previously detailed for the pellet assay. As shown in FIG. 7, TNFα was added (100 ng/ml; bars labeled with *) to some cultures in the chondrocyte pellet assay. Two inhibitors were added at various doses. One inhibitor, bisindolylmaleimide (BIS), is a pan-PKC inhibitor, reported to block the activity of all isoforms of PKC, including ζPKC (e.g., Toullec et al. (1991) *J. Biol. Chem.* 266:15771-81). The other inhibitor, chelerythrine chloride (CC), is a competitive inhibitor of the phorbol ester-binding site. CC competes for the phorbol ester-binding domain of the conventional and novel PKC family members and inhibits them; however, as the a typical PKCs (e.g., ζPKC; $Ca^{++}$-independent and diacylglycerol-independent PKCs) lack this binding domain, they are not inhibited by CC (e.g., Herbert et al. (1990) *Biochem. Biophys. Res. Commun.* 172:993-99). Cytokine (TNFα)-mediated release of proteoglycan into the media in the chondrocyte pellet assay was blocked by BIS (at 20-40 µM), but was not blocked by CC (FIG. 7), indicating that selective inhibition of ζPKC blocks cytokine-mediated proteoglycan degradation.

Example 7

ζPKC is Responsible for TNFα-Induced Activation of NF-κB in Chondrocytes

Figure 8:
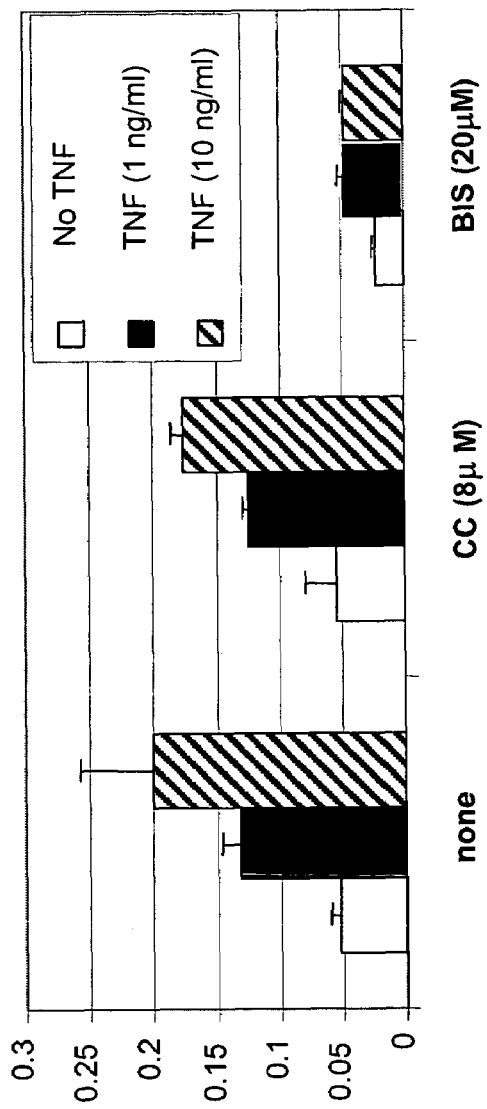
FIG. 8 shows the effects of the inhibitors BIS and CC on TNFα-induced activation of NF-κB. Activation of NF-κB was measured in an immortalized human chondrocyte cell line into which a luciferase reporter gene under the control of an NF-κB response element was introduced; activity (i.e., units on the y-axis) is expressed as "relative luciferase activity."

Activation of NF-κB was measured in an immortalized human chondrocyte cell line (C28/I2; see, e.g., Finger et al. (2003) *Arthritis Rheum.* 48:3395-403; Goldring (1994) *J. Clin. Invest.* 94:2307-16) into which a luciferase reporter gene under the control of an NF-κB response element was introduced. The cells were cultured in DMEM/Ham's F12 supplemented with 10% FBS; the cells were split into 96 wells ($1\times10^5$ cells/well) and infected with adenovirus expressing NF-κB luciferase construct (100 MOI) 24 hrs prior to assay. The chondrocytes were incubated with inhibitors in serum-free media 2 hrs prior to the addition of TNF. As shown in FIG. 8, TNFα was added (1 ng/ml or 10 ng/ml) to some cultures in the chondrocyte pellet assay. BIS (20 µM), a pan-PKC inhibitor, was added to some cultures, and CC (8 µM), a competitive inhibitor of the phorbol ester binding site in some forms of PKC (but not the a typical PKCs, e.g., ζPKC), was added to other cultures. Cytokine (TNFα)-mediated activation of NF-κB was blocked by BIS, but was not blocked by CC, indicating that selective inhibition of ζPKC blocks cytokine-mediated activation of NF-κB.

What is claimed is:

1. A method for the treatment of arthritis in a subject comprising administering to the subject by intraarticular route a compound that selectively or specifically inhibits the activity of ζPKC in a chondrocyte of the subject, wherein the compound is selected from the group consisting of siRNA molecules complementary to human ζPKC mRNA and myristoylated ζPKC pseudosubstrate peptide inhibitors, and wherein the treatment of arthritis in the subject occurs as a result of selective or specific inhibition of the activity of ζPKC in the chondrocyte of the subject.

2. The method of claim 1, wherein the arthritis is osteoarthritis.

3. The method of claim 1, wherein the siRNA molecules are selected from the group consisting of siRNA molecules shown in FIG. 1.

4. The method of claim 1, wherein the ζPKC pseudosubstrate peptide inhibitors are modified to improve cell permeability.

5. A method for the treatment of arthritis in a subject comprising administering to the subject by intraarticular route a compound that selectively or specifically inhibits the expression of ζPKC in a chondrocyte of the subject, wherein the compound is an siRNA molecule complementary to human ζPKC mRNA, and wherein the treatment of arthritis in the subject occurs as a result of selective or specific inhibition of the expression of ζPKC in the chondrocyte of the subject.

6. The method of claim 5, wherein the arthritis is osteoarthritis.

7. The method of claim 5, wherein the siRNA molecule is selected from the group consisting of siRNA molecules shown in FIG. 1.

8. A method of modulating a TNF- or IL-1-induced increase in ζPKC expression or activity in a chondrocyte in vitro, comprising contacting said chondrocyte with a compound that selectively or specifically inhibits the expression or activity of ζPKC in the chondrocyte, wherein the compound is selected from the group consisting of siRNA molecules complementary to human ζPKC mRNA and myristoylated ζPKC pseudosubstrate peptide inhibitors, and wherein the modulation of the TNF- or IL-1-induced increase in ζPKC expression or activity in the chondrocyte occurs as a result of the selective or specific inhibition of the expression or activity of ζPKC in the chondrocyte.

9. The method of claim 8, wherein the siRNA molecules are selected from the group consisting of siRNA molecules shown in FIG. 1.

10. The method of claim 8, wherein the ζPKC pseudosubstrate peptide inhibitors are modified to improve cell permeability.

11. A method of inhibiting proteoglycan degradation in a subject, comprising administering to the subject by intraarticular route a compound that selectively or specifically inhibits the expression or activity of ζPKC in a chondrocyte of the subject, wherein the compound is selected from the group consisting siRNA molecules complementary to human ζPKC mRNA and myristoylated ζPKC pseudosubstrate peptide inhibitors, and wherein the inhibition of proteoglycan degradation occurs as a result of the selective or specific inhibition of the expression or activity of ζPKC in the chondrocyte of the subject.

12. The method of claim 11, wherein the method results in amelioration of at least one symptom of arthritis in the subject.

13. The method of claim 12, wherein the arthritis is osteoarthritis.

14. The method of claim 11, wherein the siRNA molecules are selected from the group consisting of siRNA molecules shown in FIG. 1.

15. The method of claim 11, wherein the ζPKC pseudosubstrate peptide inhibitors are modified to improve cell permeability.

16. A method of modulating a TNF- or IL-1-induced increase in ζPKC expression or activity in a chondrocyte, comprising administering to a subject by intraarticular route a compound that selectively or specifically inhibits the expression or activity of ζPKC in the chondrocyte, wherein the compound is selected from the group consisting of siRNA molecules complementary to human ζPKC mRNA and myristoylated ζPKC pseudosubstrate peptide inhibitors, and wherein the modulation of the TNF- or IL-1-induced increase in ζPKC expression or activity in the chondrocyte occurs as a result of the selective or specific inhibition of the expression or activity of ζPKC in the chondrocyte.

17. The method of claim 16, wherein the siRNA molecules are selected from the group consisting of siRNA molecules shown in FIG. 1.

18. The method of claim 16, wherein the ζPKC pseudosubstrate peptide inhibitors are modified to improve cell permeability.

* * * * *